US010247814B2

(12) United States Patent
Cheung et al.

(10) Patent No.: US 10,247,814 B2
(45) Date of Patent: Apr. 2, 2019

(54) PHASE SHIFT DETECTOR PROCESS FOR MAKING AND USE OF SAME

(71) Applicant: NATIONAL INSTITUTE OF STANDARDS AND TECHNOLOGY, Gaithersburg, MD (US)

(72) Inventors: Kin P. Cheung, Rockville, MD (US); Jason T. Ryan, Frederick, MD (US); Jason Campbell, Frederick, MD (US)

(73) Assignee: NATIONAL INSTITUTE OF STANDARDS AND TECHNOLOGY, Gaithersburg, MD (US)

( * ) Notice: Subject to any disclaimer, the term of this patent is extended or adjusted under 35 U.S.C. 154(b) by 590 days.

(21) Appl. No.: 14/995,861

(22) Filed: Jan. 14, 2016

(65) Prior Publication Data

US 2016/0209275 A1    Jul. 21, 2016

Related U.S. Application Data

(60) Provisional application No. 62/105,480, filed on Jan. 20, 2015.

(51) Int. Cl.
| | | |
|---|---|---|
| *G01N 22/00* | (2006.01) | |
| *H01Q 1/52* | (2006.01) | |
| *G01S 13/00* | (2006.01) | |

(52) U.S. Cl.
CPC ............. *G01S 13/00* (2013.01); *G01N 22/00* (2013.01); *H01Q 1/521* (2013.01); *H01Q 1/526* (2013.01)

(58) Field of Classification Search
CPC ........ H01Q 1/526; H01Q 1/521; G01N 22/00; G01S 13/00
USPC ....... 324/500, 521, 600, 617, 622, 637, 683, 324/709, 200, 233, 250, 76.11, 76.14, 324/76.56
See application file for complete search history.

(56) References Cited

U.S. PATENT DOCUMENTS

| | | | |
|---|---|---|---|
| 6,552,803 B1 * | 4/2003 | Wang ................. | G01B 11/0675 356/502 |
| 8,674,705 B2 | 3/2014 | Bense et al. | |
| 2006/0125465 A1 * | 6/2006 | Xiang ................... | G01Q 60/22 324/72.5 |

* cited by examiner

*Primary Examiner* — Melissa J Koval
*Assistant Examiner* — Trung Nguyen
(74) *Attorney, Agent, or Firm* — Office of Chief Counsel for National Institute of Standards and Technology

(57) ABSTRACT

A phase shift detector includes: an interferometer; and a microwave probe in electrical communication with the interferometer, the microwave probe including: a primary shield electrode; and a transmission electrode disposed proximate to the primary shield electrode, the transmission electrode and the primary shield electrode being exposed and arranged to produce an electric field, wherein the transmission electrode is isolated electrically from the primary shield electrode.

16 Claims, 23 Drawing Sheets

PHASE SHIFT DETECTOR PROCESS FOR MAKING AND USE OF SAME

CROSS REFERENCE TO RELATED APPLICATIONS

This application claims the benefit of U.S. Provisional Patent Application Ser. No. 62/105,480, filed Jan. 20, 2015, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is a phase shift detector comprising: an interferometer to receive a microwave radiation; and a microwave probe in electrical communication with the interferometer to receive a sample microwave radiation from the interferometer and to produce a probe microwave radiation, the microwave probe comprising: a primary shield electrode; and a transmission electrode disposed proximate to the primary shield electrode, the transmission electrode and the primary shield electrode being exposed and arranged to produce an electric field in response to receipt of the sample microwave radiation by the transmission electrode, wherein the transmission electrode is isolated electrically from the primary shield electrode.

Further disclosed is a phase shift detector comprising: an interferometer comprising: a power splitter; a reference arm in electrical communication with the power splitter and comprising a phase shifter; a sample arm in electrical communication with the power splitter and comprising an attenuator; and a power combiner in electrical communication with the reference arm and the sample arm; and a microwave probe in electrical communication with the sample arm and the power combiner, the microwave probe comprising: a substrate comprising a dielectric; a primary shield electrode disposed on the substrate; a secondary shield electrode opposingly disposed to the primary shield electrode; and a transmission electrode interposed between the primary shield electrode and the secondary shield electrode, wherein the transmission electrode is isolated electrically from the primary shield electrode and isolated electrically from the secondary shield electrode.

Disclosed also is a process for acquiring phase shift data, the process comprising: receiving a microwave radiation by a power splitter; producing, by the power splitter, a reference microwave radiation and a sample microwave radiation; communicating the reference microwave radiation to a reference arm; communicating the sample radiation to a sample arm; communicating the sample radiation from the sample arm to a microwave probe, the microwave probe comprising: a substrate comprising a dielectric; a primary shield electrode disposed on the substrate; a secondary shield electrode opposingly disposed to the primary shield electrode; and a transmission electrode interposed between the primary shield electrode and the secondary shield electrode, the transmission electrode being isolated electrically from the primary shield electrode and isolated electrically from the secondary shield electrode; subjecting, by the microwave probe, a sample to the sample microwave radiation; producing, by the microwave probe, a probe microwave radiation in response to subjecting the sample to the sample microwave radiation; communicating the probe microwave radiation in a sample arm to a power combiner; receiving, by the power combiner, the probe microwave radiation and the reference microwave radiation from the reference arm; and producing, by the power combiner, an interferometer signal in response to receiving the probe microwave radiation and the reference microwave radiation to acquire phase shift data.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a phase shift detector provides detection of a phase shift by an interferometer in electrical communication with a microwave probe. An electric field is produced by the microwave probe, and a presence of a sample in the electric field can change an electrical balance between a reference arm and sample arm of the interferometer. The change can occur, e.g., because of a change in an effective dielectric constant of the sample. Moreover, the electrical balance between the reference arm and sample arm of the interferometer is controllable. It is contemplated that the microwave probe can transmit a wavelength of optical radiation such as infrared radiation so that the phase shift detector can be used in Fourier transform infrared spectroscopy.

Figure 1:
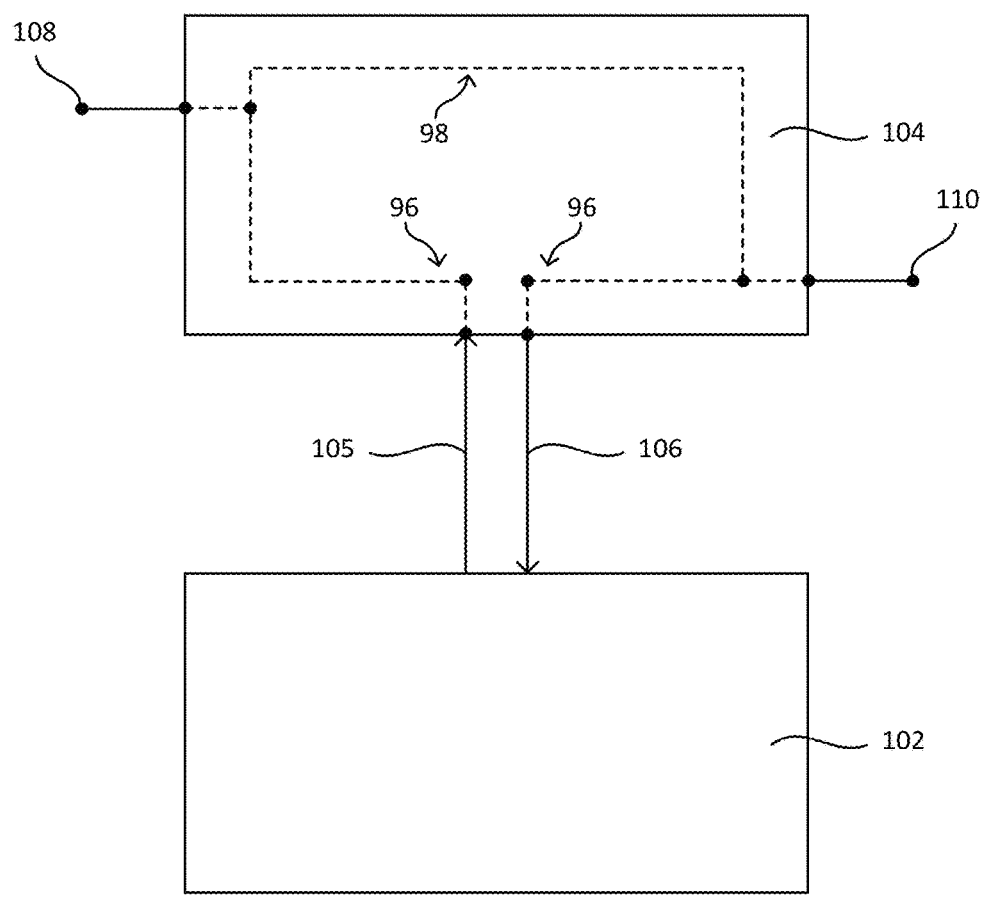
FIG. 1 shows a phase shift detector.

In an embodiment, with reference to FIG. 1, phase shift detector 100 includes microwave probe 102 in electrical communication with interferometer 104, wherein interferometer 104 receives a microwave radiation via interferometer input 108 and produces an interferometer signal at interferometer output 110. Interferometer 104 includes reference arm 98 and sample arm 96 that are in electrical communication with interferometer input 108 and interferometer output 110. Sample arm 96 includes first transmission member 105 and second transmission member 106 that electrically interconnect microwave probe 102 and sample arm 96 of interferometer 104.

Figure 2:
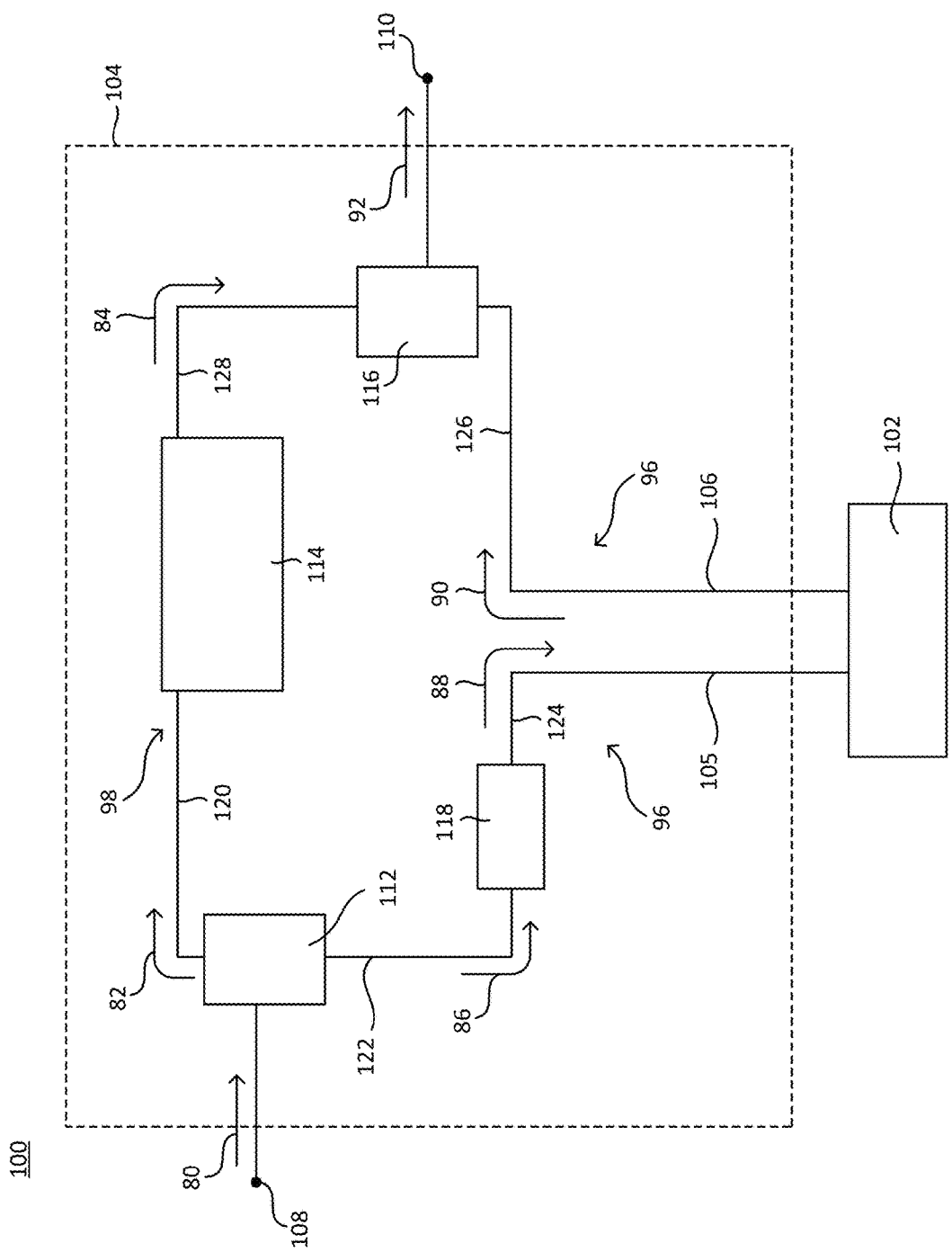
FIG. 2 shows a phase shift detector.

With reference to FIG. 2, in an embodiment of phase shift detector 100, interferometer 104 includes: power splitter 112 electrically connected to interferometer input 108; reference arm 98 in electrical communication with power splitter 112 and including phase shifter 114; sample arm 96 in electrical communication with power splitter 112 and including attenuator 118; and power combiner 116 in electrical communication with reference arm 98 and sample arm 96. Here, microwave probe 102 is in electrical communication with sample arm 96 and power combiner 116. A plurality of transmission lines (120, 122, 124, 126, 128) electrically interconnects components of phase shift detector 100.

According to an embodiment, interferometer receives microwave radiation 80 and is in electrical communication with microwave probe 102. Microwave radiation 80 includes a power and phase and having a wavelength, e.g., in the microwave region of the electromagnetic spectrum. Microwave probe 102 receives sample microwave radiation 88 from interferometer 104 and produces probe microwave radiation 90. Further interferometer 104 includes power splitter 112 to receive microwave radiation 80, wherein power splitter 112 produces reference microwave radiation 82 from microwave radiation 80 and also produces sample microwave radiation 86 from microwave radiation 80. Reference arm 98 is in electrical communication with power splitter 112 and receives reference microwave radiation 82. Sample arm 96 receives sample microwave radiation 86 from power splitter 112 and communicates sample microwave radiation 88 to microwave probe 102. In some embodiments, reference microwave radiation 82 includes a first phase and a first power. Sample microwave radiation 86 includes the first phase and a second power.

Reference arm 98 includes phase shifter 114 to receive reference microwave radiation 82 that includes the first phase and to shift the first phase to a second phase. Phase shifter 114 produces and communicates reference microwave radiation 84 that includes the second phase.

Sample arm 96 includes attenuator 118 to receive sample microwave radiation 86 that includes the second power. Attenuator 118 attenuates the second power to a third power and produces sample microwave radiation 88 that includes the third power. Microwave probe 102 receives sample microwave radiation 88 from attenuator 118.

In a certain embodiment, attenuator 118 is connected electrically between microwave probe 102 and power combiner 116 rather than attenuating the second power of sample microwave radiation 86. In some embodiments, a first attenuator is electrically interposed between splitter 112 and microwave probe 102, and a second attenuator is electrically interposed between microwave probe 102 and power combiner 116. In a particular embodiment, reference arm 98 includes a third attenuator electrically interposed between splitter 112 and power combiner 116. A phase shifter can be included in sample 96 or optionally absent in reference arm 98.

According to an embodiment, sample arm 96 includes first transmission member 105 electrically interposed between attenuator 118 and microwave probe 102 and in electrical communication with attenuator 118 to provide sample microwave radiation 88 to microwave probe 102. Microwave probe 102 produces probe microwave radiation 90 response to receipt of sample microwave radiation 88. Sample arm 96 further can include second transmission member 106 in electrical communication with microwave probe 102 to receive probe microwave radiation 106 from microwave probe 102.

Power combiner 116 of interferometer 104 is in electrical communication with reference arm 98 and sample arm 96 and receives reference microwave radiation 84 from reference 98 arm and also receives probe microwave radiation 90 from second transmission member 106 of sample arm 96. In response to receiving reference microwave radiation 84 and probe microwave radiation 90, power combiner 116 interferometrically produces interferometer signal 92 at interferometer output 110. It is contemplated that phase shifter 114 or attenuator 118 are controlled to adjust respectively a relative phase or amplitude of reference microwave radiation 84 or probe microwave radiation 90 such that reference arm 98 can be electrically balanced with sample arm 96. In electrical balance, e.g., in an absence of a sample in an electrical field produced by microwave probe 102, interferometer signal 92 produced by power combiner 116 can be substantially a direct current (DC) voltage with substantially zero amplitude, i.e., having the potential of zero volts DC (0 VDC). Without wishing to be bound by theory, electrically balancing reference microwave radiation 84 against probe microwave radiation 90 occurs by superposition (also referred to as interference) of their waveforms such that when reference microwave radiation 84 and probe microwave radiation 90 have a substantially similar amplitude but are 180° out of phase, reference arm 98 is balanced against sample arm 96, and interferometer signal 92 is substantially zero amplitude. On the other hand, when reference microwave radiation 84 and probe microwave radiation 90 have different amplitudes or not out-of-phase, reference arm 98 is unbalanced against sample arm 96, and interferometer signal 92 has a non-zero amplitude, e.g., a voltage amplitude (root-mean square alternating current or DC) of several nanovolts (nV), microvolts (µV), millivolts (mV), or the like.

According to an embodiment, components (e.g., sample arm 96, reference arm 98, Phase shift detector 100, first transmission member 105, second transmission member 106, interferometer input 108, interferometer output 110, power splitter 112, phase shifter 114, power combiner 116, attenuator 118, transmission line (120, 122, 124, 126, 128), or the like) of interferometer 104 independently can be free-standing or mounted on a support. In an embodiment, components are mounted on a support such as an optical breadboard, printed circuit board, and the like. For the printed circuit board, the plurality of transmission lines (120, 122, 124, 126, 128) electrically interconnects components of interferometer 104 and can be wire traces disposed on the printed circuit board. In a certain embodiment, transmission lines (120, 122, 124, 126, 128) are electrical cables (e.g., coaxial cable) that electrically interconnect components of interferometer 104 via electrical connector such as an SMA connector, BNC connector, or the like.

Interferometer 104 can be configured to perform various types of interferometry among reference microwave radiation 84 and probe microwave radiation 90. In an embodiment, interferometer 104 is configured as a Mach-Zehnder interferometer, wherein reference arm 98 communicates reference microwave radiation 84 to power combiner 116 and sample arm 96 communicates probe microwave radiation 92 power combiner 116, and power combiner 116 produces interferometer signal 92 from superposition of reference microwave radiation 84 and probe microwave radiation 90. Other exemplary interferometer configurations of interferometer 104 include a Michelson interferometer in which the microwave in each arm of the Michelson interferometer is reflected back into the incoming path; a Sagnac interferometer in which the two arms of the Sagnac interferometer form a closed counter-propagating loop so the waves re-combine at an original splitter; and the like.

In an embodiment, power splitter 112 includes a three ports device that divides input microwave radiation 80 into two outputs 82 and 122. Power splitter 112 can be a resistive tee with one resistor connected to two resistors to form a branching tee. Resistor values are chosen for a selected impedance value. It is simple, low cost and wide bandwidth. Two outputs are 180 degrees out-of-phase to each other, which can be advantageous.

In an embodiment, phase shifter 114 is a two ports device that can change a phase of output microwave 128 while input 98 remains constant. Exemplary phase shifters include a delay line that adjusts a path length of propagation for the microwave; a phase shifter based on a varactor can provide continuous phase shift by voltage control; a ferroelectric phase shifter using electrically tunable dielectric constant (and therefore propagation velocity) to provide voltage controlled phase shift; and the like.

In an embodiment, power combiner 116 is a three ports device that takes two incoming microwave radiations 84, 126 and combines them into one output 92. Power combiner 116 can be a power splitter working in reverse.

In an embodiment, attenuator 118 is a two ports device in which input microwave radiation 86 is present at output 124 with a predetermined reduction in power. An exemplary attenuator is a power splitter that includes a resistor tee with one output arm internally shunt to ground. Attenuator 118 can include a plurality of resistors to provide broad band attenuation, e.g., a Pi attenuator in which the input microwave power flows through one resistor that has its input and output end connected to ground through a resistor each. Another example is a bridged-tee configuration in which a fourth resistor connects the input and output ports of a resister tee, which advantageously provides fine control of the attenuation factor.

Phase shift detector 100 can include additional or alternative components. Interferometer 104 can include, e.g., a filter (a bandpass filter and the like) and the like. The bandpass filter can be disposed before input 108 of interferometer 104 to purify the microwave radiation (suppress noise) to increase the detector sensitivity.

According to an embodiment, phase shift detector 100 includes a radiation source in electrical communication with interferometer input 108 and provides microwave radiation 80 to interferometer 104. Exemplary radiation sources include a frequency synthesizer to cover a range of microwave frequencies and control its amplitude; dielectric resonance oscillator tunable over a (e.g., very small) range of microwave frequencies; voltage-controlled oscillator that covers a relatively broad frequency band and provides frequency to be rapidly changed by a control voltage.

In an embodiment, interferometer input 108 receives microwave radiation 80 and provides microwave radiation 80 to splitter 112. Interferometer input 108 can be an SMA connector that can handle the microwave frequencies used; type N connector that can handle microwave frequency at higher power; microwave connector such as 2.9 mm connector appropriate for the frequency used; and the like.

In an embodiment, interferometer output 110 receives interferometer signal 92 and can provide interferometer signal 92 to an external device (e.g., an oscilloscope, data acquisition card, field programmable gate array, computer, and the like). Interferometer output can be a microwave connector such as an SMA connector that can handle the frequency and power used.

In an embodiment, transmission lines (120, 122, 124, 126, 128) and transmission member (105, 106) electrically communicate electromagnetic radiation having a frequency (e.g., megahertz, gigahertz, and the like) effective to produce the electric field between electrodes (e.g., transmission electrode 152, primary shield electrode 150, and secondary shield electrode 154) of the microwave probe 102. Transmission member (105, 106) can be a wire trace (e.g., on a PCB), cable, and the like. According to an embodiment, transition member (105, 106) is the cable. In a particular embodiment, the cable includes a coaxial cable, and with reference to FIG. 2 and FIG. 3, first transmission member 105 is electrically interposed between attenuator 118 and microwave probe 102 and is in electrical communication with attenuator 118 to receive and communicate sample microwave radiation 88 to microwave probe 102. First transmission member 105 includes first central conductor 300 to receive sample microwave radiation 88 from attenuator 118 and in electrical communication with transmission electrode 152 of microwave probe 102 to communicate sample microwave radiation 88 to transmission electrode 102. First transmission member 105 also includes first shield conductor 304 surroundingly disposed about first central conductor 300 and in electrical communication with primary shield electrode 150 of microwave probe 102. First shield conductor 304 also can be in electrical communication with secondary shield electrode 154 of microwave probe 102 such that primary shield electrode 150 and secondary shield electrode 154 have a substantially identical electrical potential as first shield conductor 304. First dielectric sheath 302 is interposed between first central conductor 300 and first shield conductor 304 to isolate electrically first central conductor 300 from first shield conductor 304.

According to an embodiment, second transmission member 106 is in electrical communication with microwave probe 102 to receive probe microwave radiation 90 from microwave probe 102. Second transmission member 106 can include second central conductor 306 in electrical communication with transmission electrode 152 of microwave probe 102, second shield conductor 310 surroundingly disposed about second central conductor 306 and in electrical communication with secondary shield electrode 154 of microwave probe 102, and second dielectric sheath 308 interposed between second central conductor 306 and second shield conductor 310 to isolate electrically second central conductor 306 from second shield conductor 310. Second shield conductor 310 also can be in electrical communication with primary shield electrode 150 of microwave probe 102 such that primary shield electrode 150 and secondary shield electrode 154 have a substantially identical electrical potential as second shield conductor 310, wherein first shield conductor 304 of first transmission member 105 is in electrical communication with second shield conductor 310 of second transmission member 106 via primary shield electrode 150 and secondary shield electrode 154 of microwave probe 102. Moreover, it should be appreciated that first central conductor 300 of first transmission member 105 is in electrical communication with second central conductor 306 of second transmission member 106 via primary shield electrode 150 of microwave probe 102.

Electrical connections between first transmission member 105, probe 102, and second transmission member 106 can include a solder connection, spot weld, continuous metal trace, electrically conductive adhesive (e.g., silver paste and the like) and the like. In an embodiment, a plurality of conductor members (312, 314, 316, 318, 320, 322) are electrically conductive and electrically connect first transmission member 105, probe 102, and second transmission member 106.

Figure 3:
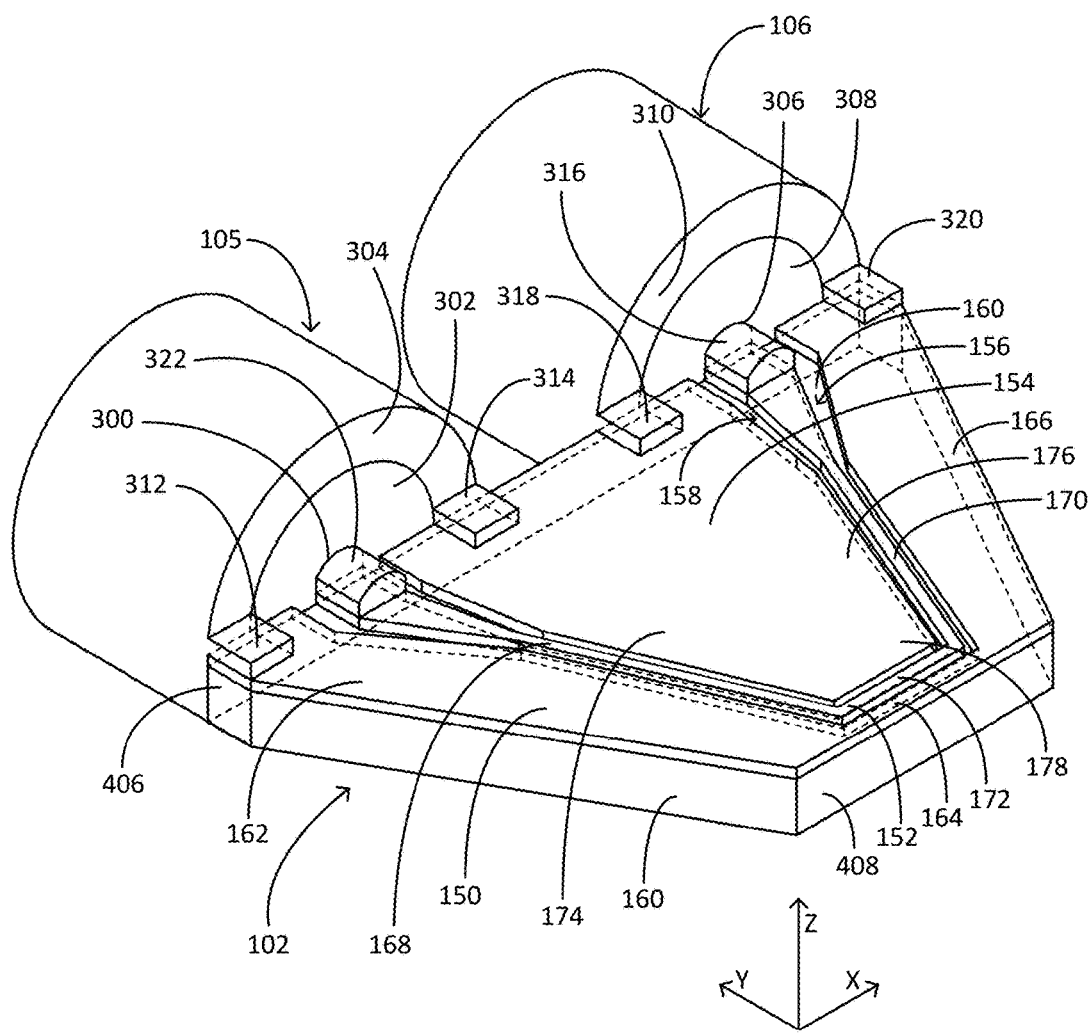
FIG. 3 shows a perspective view of a microwave probe connected to a first transmission member and a second transmission member of a portion of a phase shift detector.
Figure 4:
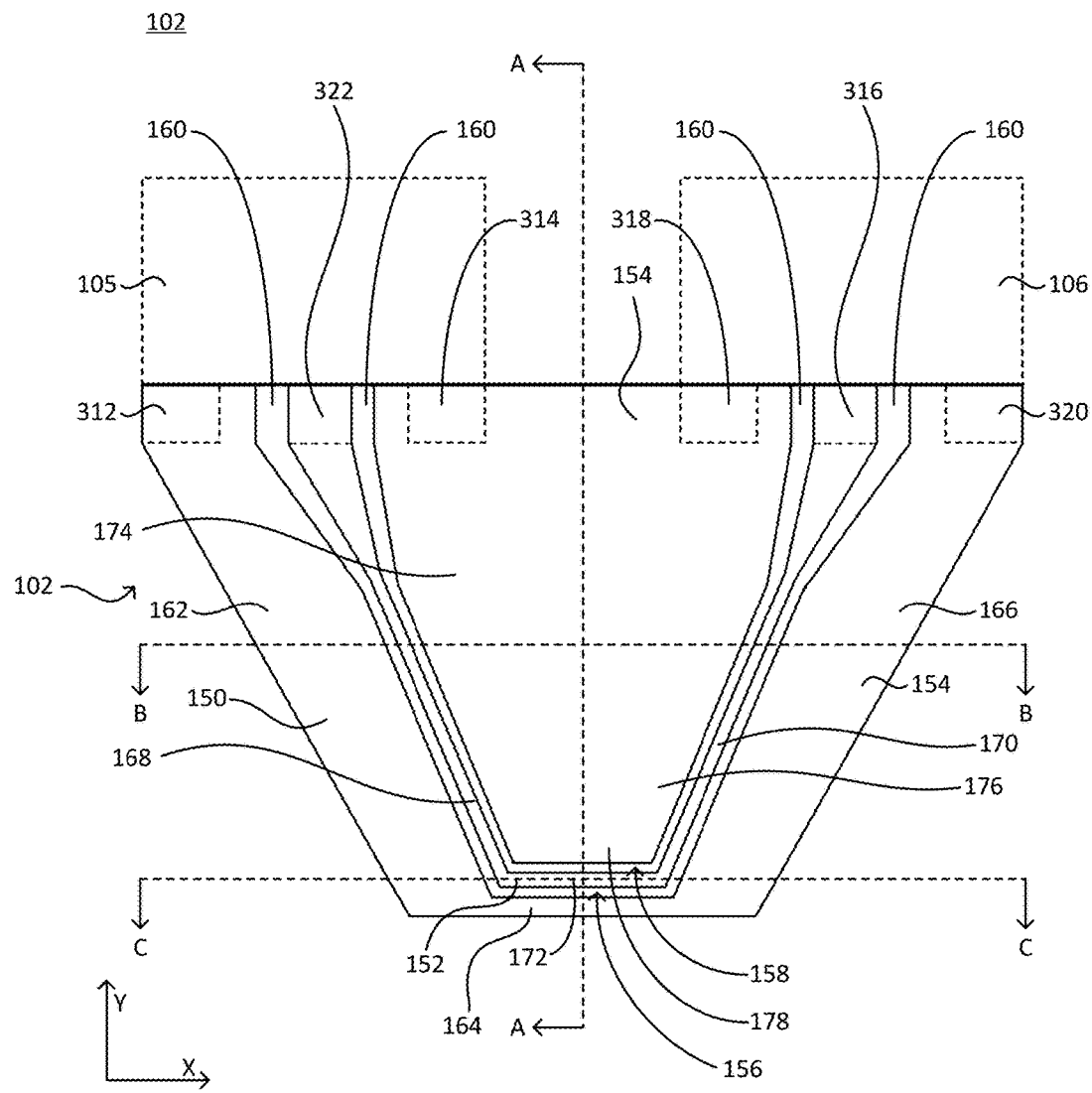
FIG. 4 shows a top view of the microwave probe shown in FIG. 3.
Figure 5:
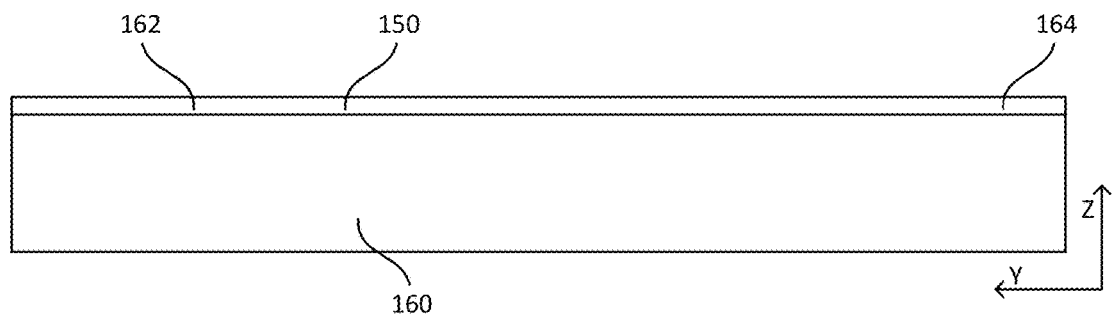
FIG. 5 shows a side of the microwave probe shown in FIG. 3.
Figure 6:
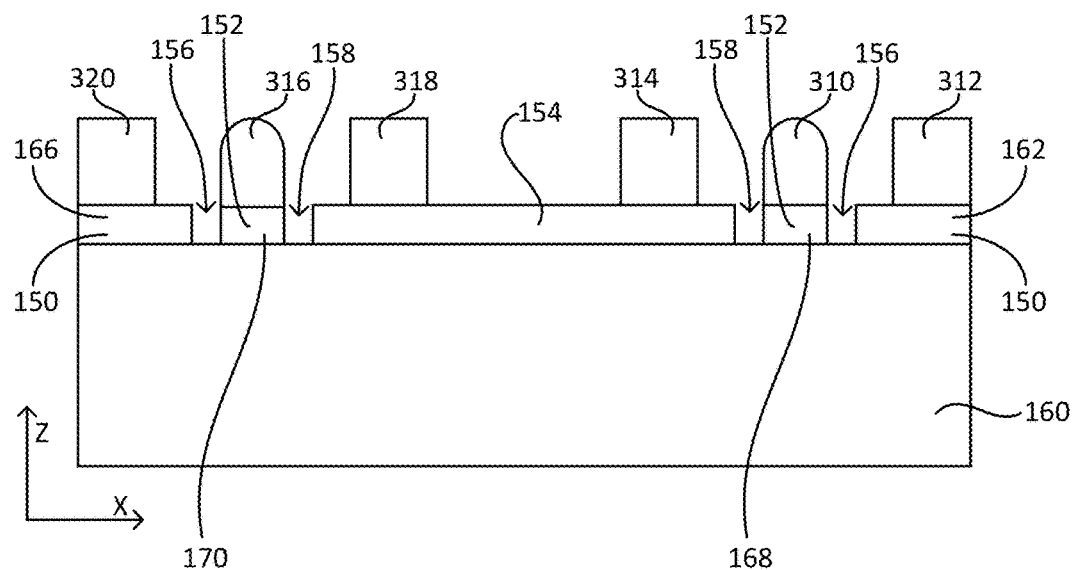
FIG. 6 shows a first end view of the microwave probe shown in FIG. 3.
Figure 7:
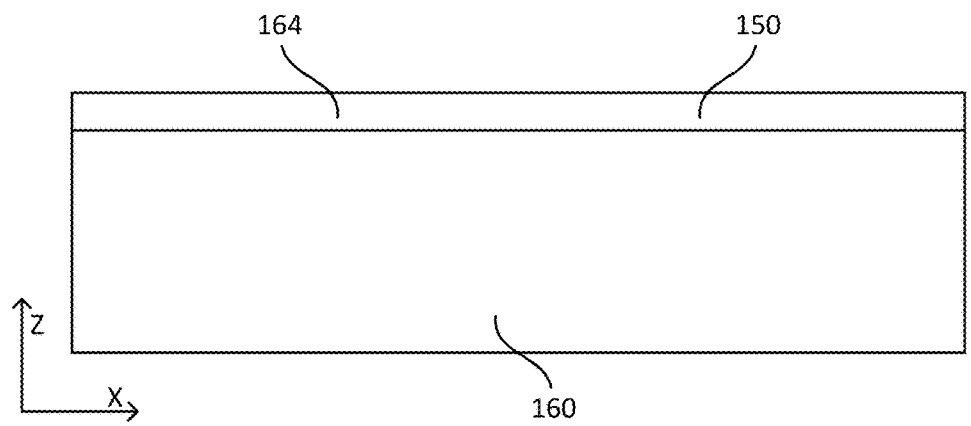
FIG. 7 shows a second end view of the microwave probe shown in FIG. 3.
Figure 8:
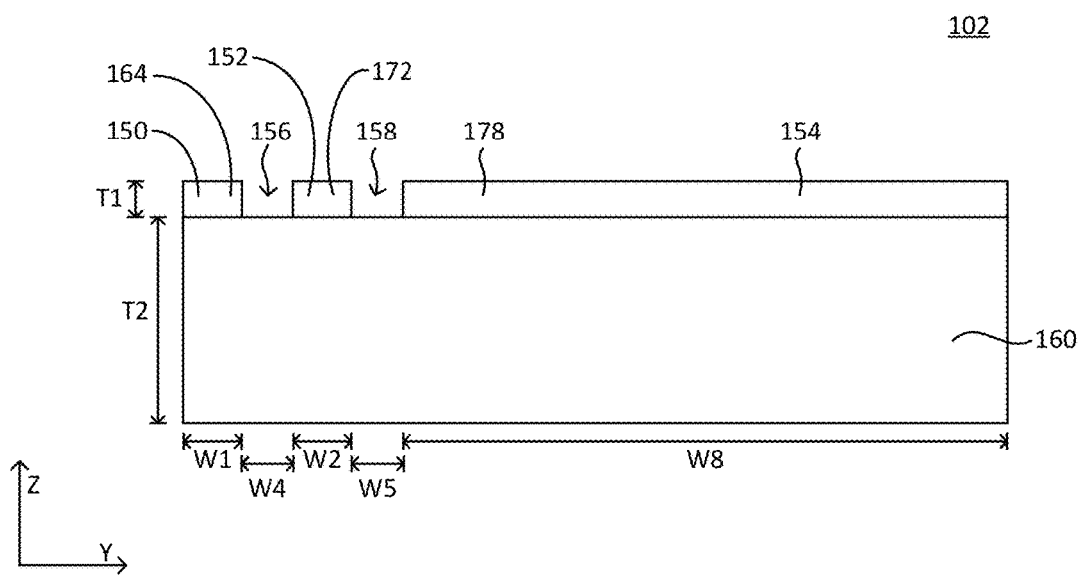
FIG. 8 shows a cross-section along line A-A of the microwave probe shown in FIG. 3.

Microwave probe 102 receives sample microwave radiation 88 from interferometer 104 and produces probe microwave radiation 90. An embodiment of microwave probe 100 is shown in FIG. 3 (a perspective view of microwave probe 102 of phase shift detector 100), FIG. 4 (a top view of microwave probe 102 shown in FIG. 3), FIG. 5 (a side of microwave probe 102 shown in FIG. 3), FIG. 6 (a first end view of microwave probe 102 shown in FIG. 3), FIG. 7 (a second end view of microwave probe 102 shown in FIG. 3), FIG. 8 (a cross-section along line A-A of microwave probe 102 shown in FIG. 3), FIG. 9 (a cross-section along line B-B of microwave probe 102 shown in FIG. 3), and FIG. 10 (a cross-section along line C-C of microwave probe 102 shown in FIG. 3). Here, microwave probe 102 includes primary shield electrode 150 and transmission electrode 152 disposed proximate to primary shield electrode 150, wherein transmission electrode 152 and primary shield electrode 150 are exposed and arranged to produce an electric field in response to receipt of sample microwave radiation 88 from first transmission member 105 by transmission electrode. Transmission electrode 152 is isolated electrically from primary shield electrode 150. In some embodiments, microwave probe 102 further includes secondary shield electrode 154 disposed proximate to transmission electrode 152 such that transmission electrode 152 is interposed between secondary shield electrode 154 and primary shield electrode 150. Moreover, first electrode gap 156 separates primary shield electrode 150 from transmission electrode 152 such that primary shield electrode 152 is spaced apart from transmission electrode 152. Second electrode gap 158 separates secondary shield electrode 154 from transmission electrode 152 such that secondary shield electrode 154 is spaced apart from transmission electrode 152. Further, transmission electrode 152 is isolated electrically from secondary shield electrode 154, wherein secondary shield electrode 154 is exposed and arranged to produce an electric field between secondary shield electrode 154 and transmission electrode 152 in response to receipt of sample microwave radiation 88 from first transmission member 105 by transmission electrode 152.

According to an embodiment, microwave probe 102 includes substrate 160 upon which transmission electrode 152, primary shield electrode 150, and secondary shield electrode 154 are disposed.

A shape or geometrical pattern of primary shield electrode 150, transmission electrode 152, and secondary shield electrode 154 independently can be selected to produce the electric field between transmission electrode 152 and shield electrodes (150, 154). Exemplary shapes include a round shape, linear shape, open polygonal shape (having opposing ends connected to first transmission member 105 and second transmission member 106), U-shape, V-shape, serpentine, interdigitate, and the like. In an embodiment, primary shield electrode 150 includes a plurality of portions such as first lateral shield electrode 162 in electrical communication with first shield conductor 304 of first transmission member 105, first lateral shield electrode 166 in electrical communication with second shield conductor 310 of second transmission member 106, and first terminal shield electrode 164 interposed between and in electrical communication with first lateral shield electrodes (162, 166).

According to an embodiment, transmission electrode 152 includes a plurality of portions such as lateral transmission electrode 168 in electrical communication with first central conductor 300 of first transmission member 105, lateral transmission electrode 170 in electrical communication with second central conductor 306 of second transmission member 106, and terminal transmission electrode 172 interposed between and in electrical communication with lateral transmission electrodes (168, 170).

In an embodiment, secondary shield electrode 154 includes a plurality of portions such as second lateral shield electrode 174 in electrical communication with first shield conductor 304 of first transmission member 105, second lateral shield electrode 176 in electrical communication with second shield conductor 310 of second transmission member 106, and second terminal shield electrode 178 interposed between and in electrical communication with second lateral shield electrodes (174, 176).

First electrode gap 156 separates and is interposed between transmission electrode 152 (particularly, lateral transmission electrode (168, 170) and terminal transmission electrode 172) and primary shield electrode 150 (particularly, first lateral shield electrode 162, 166 and first terminal shield electrode 164) to electrically isolate transmission electrode 152 from primary shield electrode 150.

Second electrode gap 158 separates and is interposed between transmission electrode 152 (particularly, lateral transmission electrode (168, 170) and terminal transmission electrode 172) and secondary shield electrode 154 (particularly, second lateral shield electrode 174, 176 and second terminal shield electrode 178) to electrically isolate transmission electrode 152 from secondary shield electrode 154.

In a certain embodiment, interferometer 104 and microwave probe 102 physically are separate components of 100 and are interconnected and in electrical communication via first transmission member 105 and second transmission member 106, e.g., as shown in FIG. 3. Interferometer 104 and microwave probe 102 can be rigidly or flexibly interconnected. According to an embodiment, interferometer 104 and microwave probe 102 are interconnected rigidly such that motion of microwave probe 102 and interferometer 104 are coupled, wherein movement of interferometer 104 produces movement in microwave probe 102. In a certain embodiment, interferometer 104 and microwave probe 102 are interconnected flexibly such that motion of microwave probe 102 and interferometer 104 are independent, wherein movement of microwave probe 102 occurs independently of movement of interferometer 104. It is contemplated that a position of microwave probe 102 can be stationary or variable in a laboratory frame of reference or with respect to the sample. Movement of microwave probe 102 can be automated or can be manual.

Figure 11:
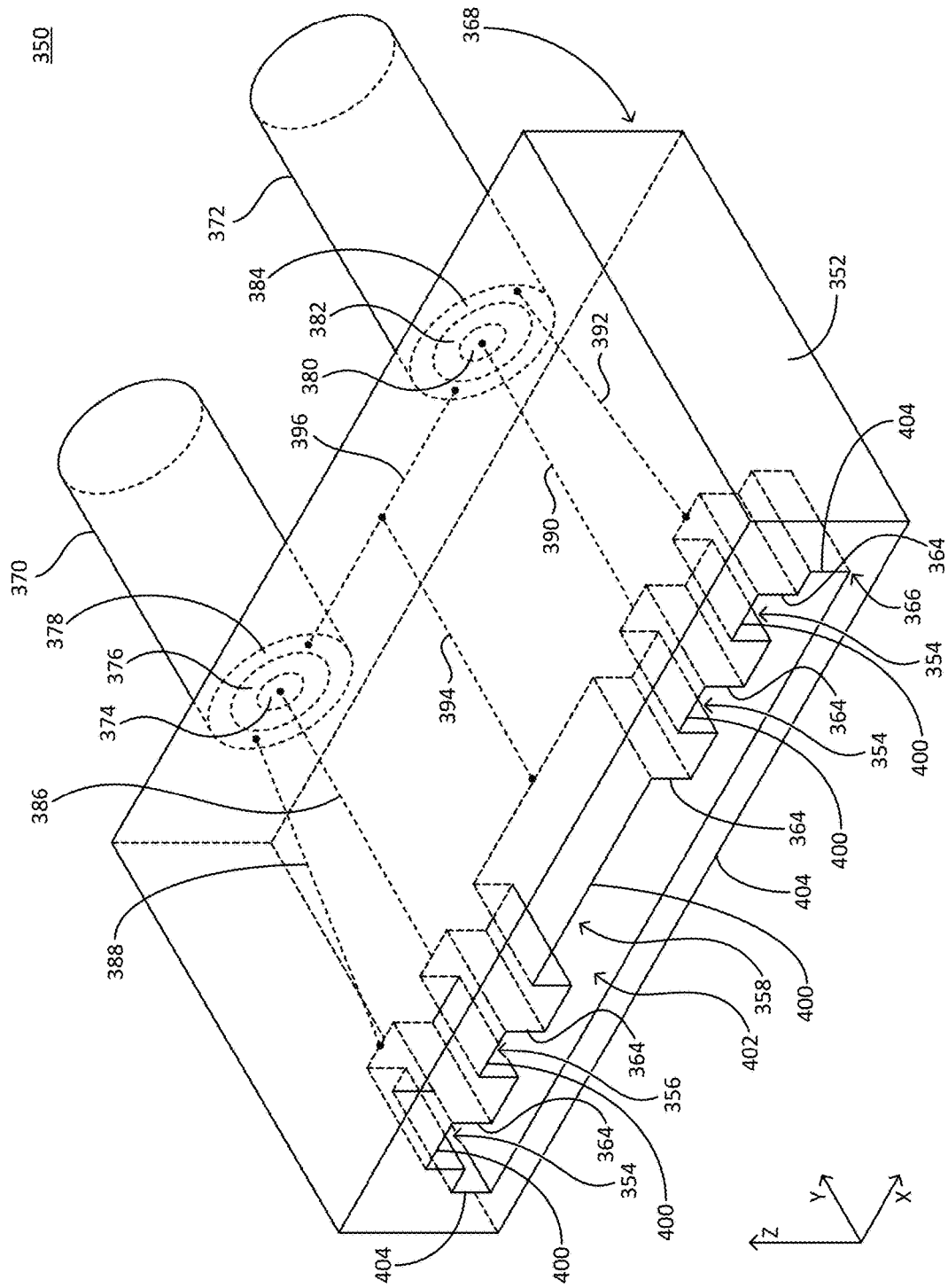
FIG. 11 shows a perspective view of an interface coupler.
Figure 12:
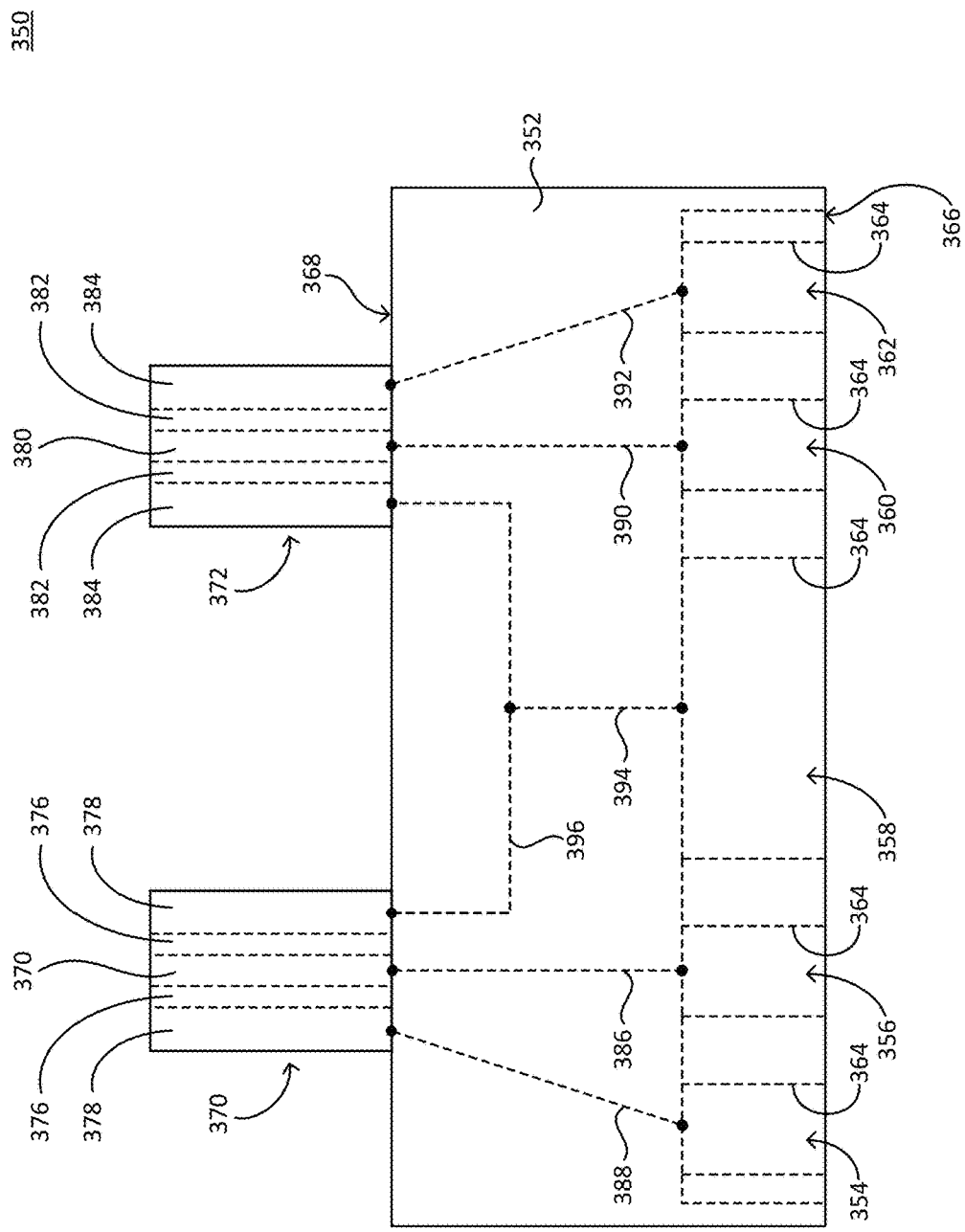
FIG. 12 shows a top view of the interface coupler shown in FIG. 11.
Figure 13:
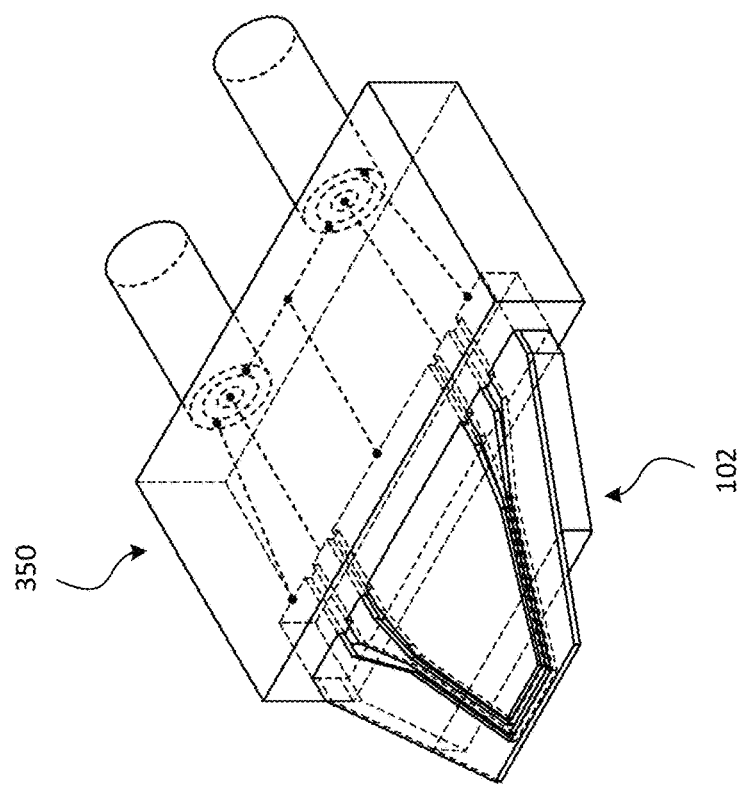
FIG. 13 shows a perspective view (left figure: solid outer surface; right figure: dashed lines showing internal structure or electrical connections) of the interface coupler shown in FIG. 11 connected to a microwave probe.
Figure 13:
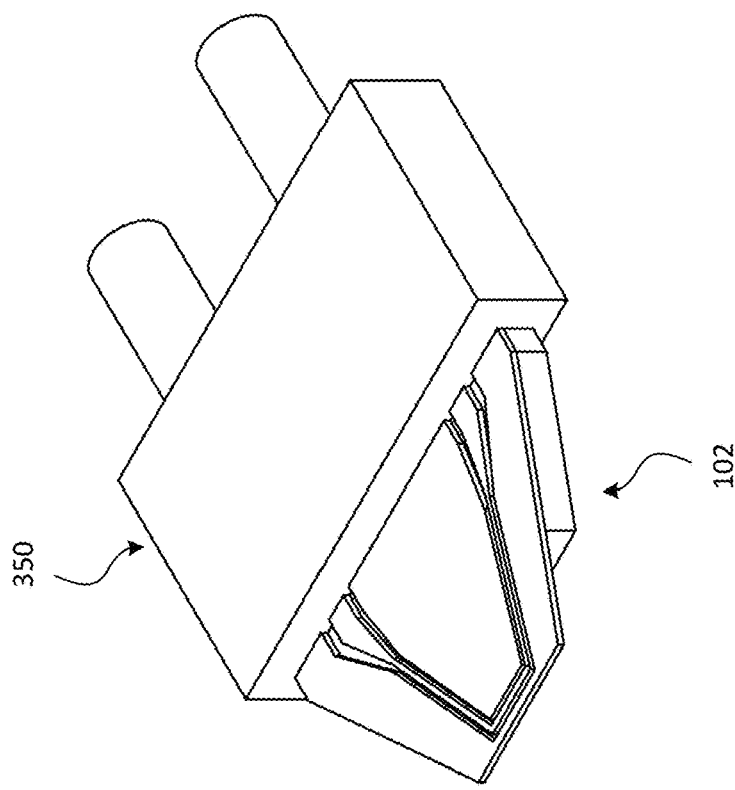

According to an embodiment, with reference to FIG. 11 (perspective view of interface coupler 350), FIG. 12 (top view of interface coupler 350), and FIG. 13 (perspective view of interface coupler 350 connected to microwave probe 102, first transmission member 105, and second transmission member 106), phase shift detector 100 includes interface coupler 350 electrically interposed between the sample arm 96 and microwave probe 102. Interface coupler 350 can include a body 352 (e.g., an electrically insulating material such as a plastic, ceramic, and the like), receiver 404 disposed in body 352 to receive second end 406 of microwave probe 102, connector 370 disposed on body 352 to connect to first transmission member 105, and connector 372 disposed on body 352 to connect to second transmission member 106. Receiver 404 of interface coupler 350 includes receiver cavity 402 to receive substrate 160 of microwave probe 102, receiver cavity 354 to receive first lateral shield electrode 162 of primary shield electrode 150 of microwave probe 102, receiver cavity 356 to receive lateral transmission electrode 168 of transmission electrode 152 of microwave probe 102, receiver cavity 358 to receive secondary shield electrode 154 of microwave probe 102, receiver cavity 360 to receive lateral transmission electrode 170 of transmission electrode 152 of microwave probe 102, and receiver cavity 362 to receive first lateral shield electrode 166 of primary shield electrode 150 of microwave probe 102.

Additionally, receiver cavity (402, 354, 356, 358, 360, 362) is bounded by wall 364 of receiver 404. Connector 370 includes outer conductor 378, central conductor 374 disposed in outer conductor 378, and dielectric insulator 376 interposed between outer conductor 378 and central conductor 374 to electrically isolate outer conductor 378 and central conductor 374. Outer conductor 378 mates with first shield conductor 304 of first transmission member 105. Central conductor 374 mates with first central conductor 300 of first transmission member 105. Similarly, connector 372 includes outer conductor 384, central conductor 380 disposed in outer conductor 384, and dielectric insulator 382 interposed between outer conductor 384 in central conductor 380 to electrically isolate outer conductor 384 and central conductor 380. Outer conductor 378 mates with first shield conductor 304 of first transmission member 105. Central conductor 374 mates with first central conductor 300 of first transmission member 105.

Receiver cavity 354 includes surface 400 that is electrically conductive (e.g., a metallic coating on wall 364) and is in electrical communication with primary shield electrode 150 via electrical conductor 388 (e.g., a wire, trace, and the like) that connects to outer conductor 378 of connector 370.

Receiver cavity 356 includes surface 400 that is electrically conductive and is in electrical communication with transmission electrode 152 via electrical conductor 386 that connects to inner conductor 374 of connector 370. Receiver cavity 358 includes surface 400 that is electrically conductive and is in electrical communication with primary shield electrode 150 via electrical conductors (394, 396) that connect to outer conductor 378 of connector 370 and outer conductor 384 of connector 372. Receiver cavity 360 includes surface 400 that is electrically conductive and is in electrical communication with transmission electrode 152 via electrical conductor 390 that connects to inner conductor 380 of connector 372. Receiver cavity 362 includes surface 400 that is electrically conductive and is in electrical communication with primary shield electrode 150 via electrical conductor 392 that connects to outer conductor 384 of connector 372. It should be appreciated that connector 370 communicate sample microwave radiation 88 from sample arm 96 of interferometer 104 to microwave probe 102. Further, connector 372 communicates probe microwave radiation 90 from microwave probe 102 to sample arm 96 of interferometer 104.

In an embodiment, interferometer 104 and microwave probe 102 are integrated, so that phase sensitive detector 100 is a monolithic structure. Here, transmission line 124 of interferometer 104 can directly connect to microwave probe 102, and transmission line 126 can directly connect to microwave probe 102.

Figure 14:
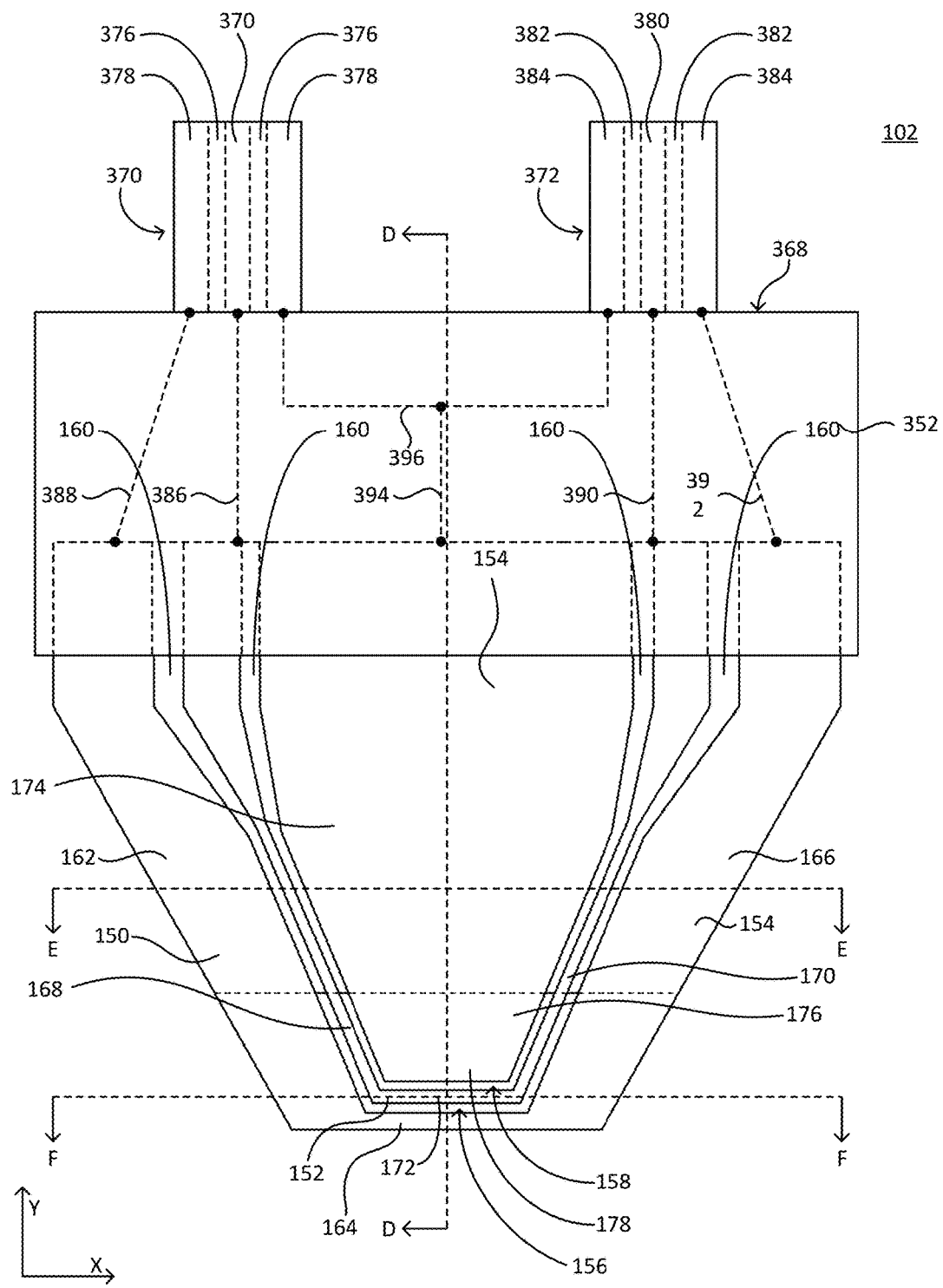
FIG. 14 shows a top view of a microwave probe connected to interface coupler of a portion of a phase shift detector.
Figure 15:
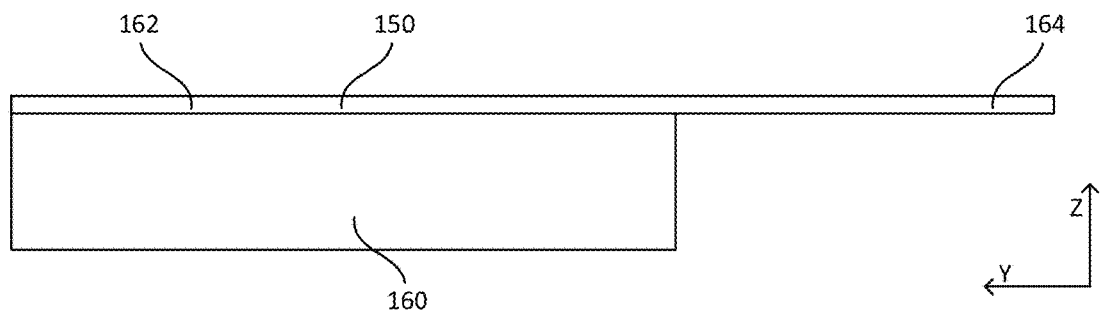
FIG. 15 shows a side of the microwave probe shown in FIG. 14.
Figure 16:
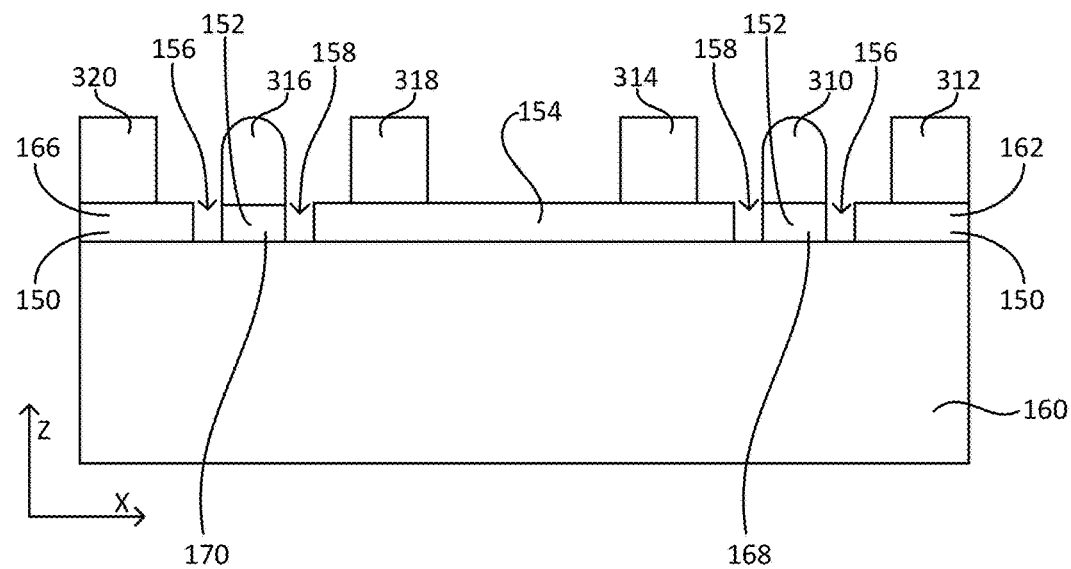
FIG. 16 shows a first end view of the microwave probe shown in FIG. 14.
Figure 17:
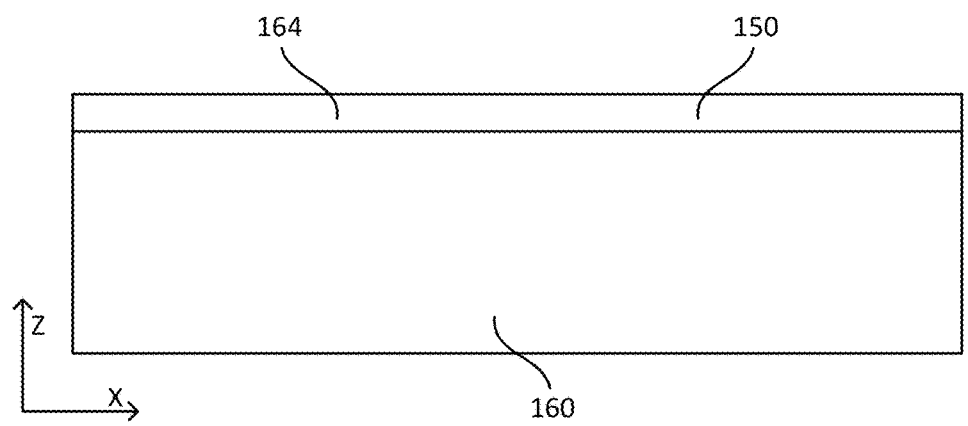
FIG. 17 shows a second end view of the microwave probe shown in FIG. 14.
Figure 18:
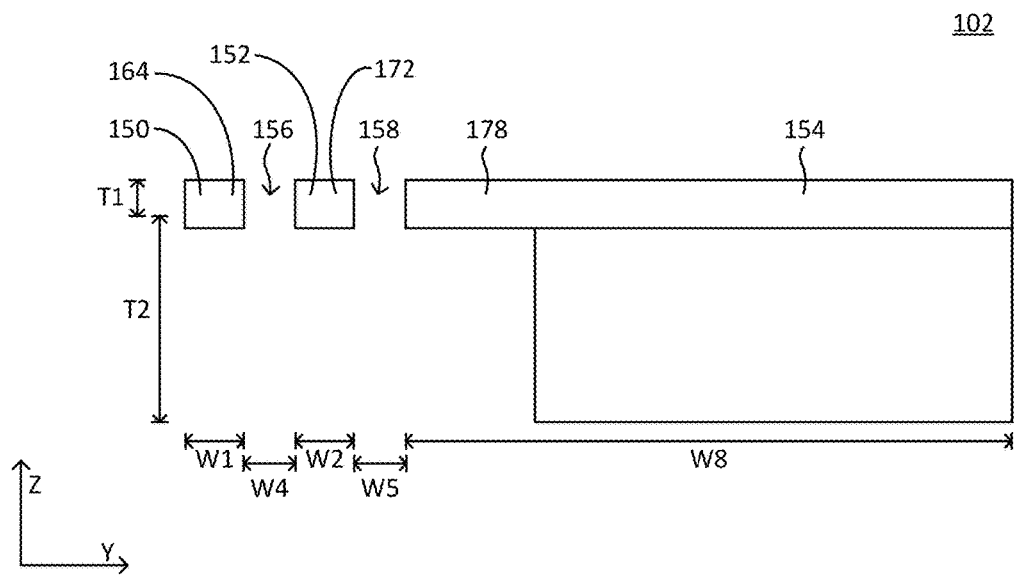
FIG. 18 shows a cross-section along line D-D of the microwave probe shown in FIG. 14.
Figure 19:
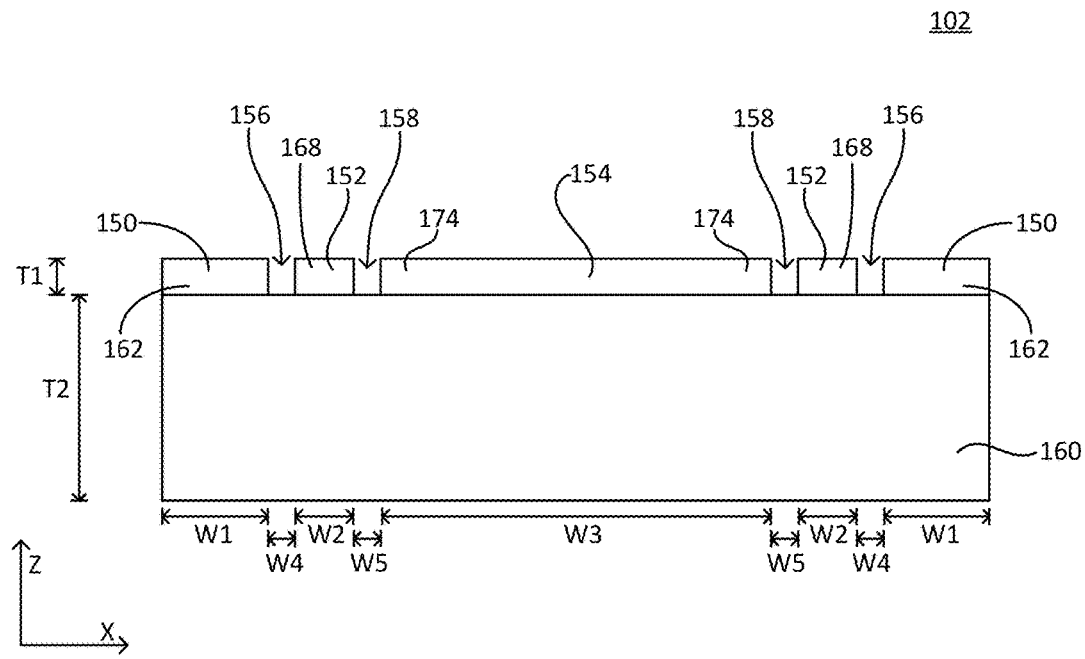
FIG. 19 shows a cross-section along line E-E of the microwave probe shown in FIG. 14.
Figure 20:
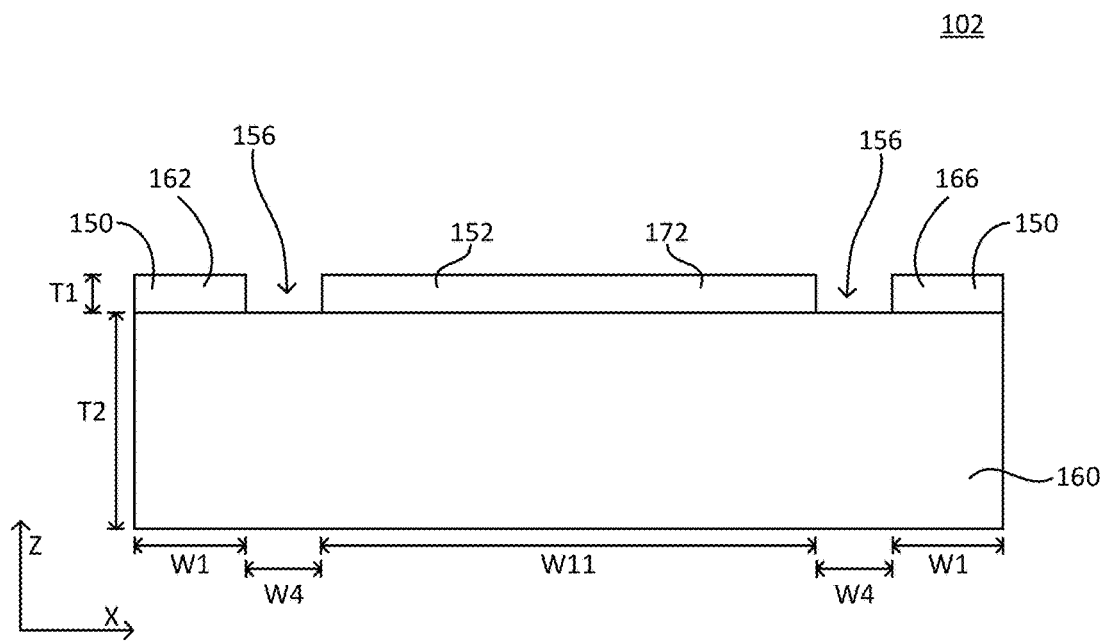
FIG. 20 shows a cross-section along line F-F of the microwave probe shown in FIG. 14.

According to an embodiment, microwave probe 102 includes substrate 160 upon which transmission electrode 152, primary shield electrode 150, and secondary shield electrode 154 are disposed. Although microwave probe 102 shown in FIG. 3 shows substrate 160 extends from second end 406 to first end 408, substrate 160 can be provided to extend over a selected, partial portion of microwave probe 102 such that a portion of primary shield electrode 150, transmission electrode 152, or secondary shield electrode 154 is not disposed on substrate 160 as shown in FIG. 14 (a top view of microwave probe 102 of phase shift detector 100), FIG. 15 (a side of microwave probe 102 shown in FIG. 14), FIG. 16 (a first end view of microwave probe 102 shown in FIG. 14), FIG. 17 (a second end view of microwave probe 102 shown in FIG. 14), FIG. 18 (a cross-section along line D-D of microwave probe 102 shown in FIG. 14), FIG. 19 (a cross-section along line E-E of microwave probe 102 shown in FIG. 14), and FIG. 20 (a cross-section along line F-F of microwave probe 102 shown in FIG. 14). Here, substrate 160 extends from second end 406 of microwave probe 102 and terminates before second terminal shield electrode 178, terminal transmission electrode 172, and first terminal shield electrode 164. In this manner, first electrode gap 156 and second electrode gap 158 in absence of substrate 160 is optically accessible for propagating a light (e.g., a laser beam or diffuse light) in first electrode gap 156 or second electrode gap 158, i.e., between second terminal shield electrode 178, terminal transmission electrode 172, and first terminal shield electrode 164, e.g., along a z-axis shown in FIG. 14 and FIG. 15.

In an embodiment, substrate 160 extends substrate 160 extends from second end 406 to first end 408 of microwave probe 102 so that substrate 160 terminates, e.g., coextensivly with second terminal shield electrode 178 such that terminal transmission electrode 172, first terminal shield electrode 164, and second terminal shield electrode 178 are disposed on substrate 160. Here, substrate 160 can be a material that is electrically insulating and also transmits light of a selected wavelength, e.g., infrared radiation. In this manner, first electrode gap 156 and second electrode gap 158 in presence of substrate 160 are optically accessible to propagate light (e.g., a laser beam or diffuse light) through substrate 160 and in first electrode gap 156 or second electrode gap 158, i.e., between second terminal shield electrode 178, terminal transmission electrode 172, and first terminal shield electrode 164, e.g., along the z-axis shown in FIG. 3.

Figure 21:
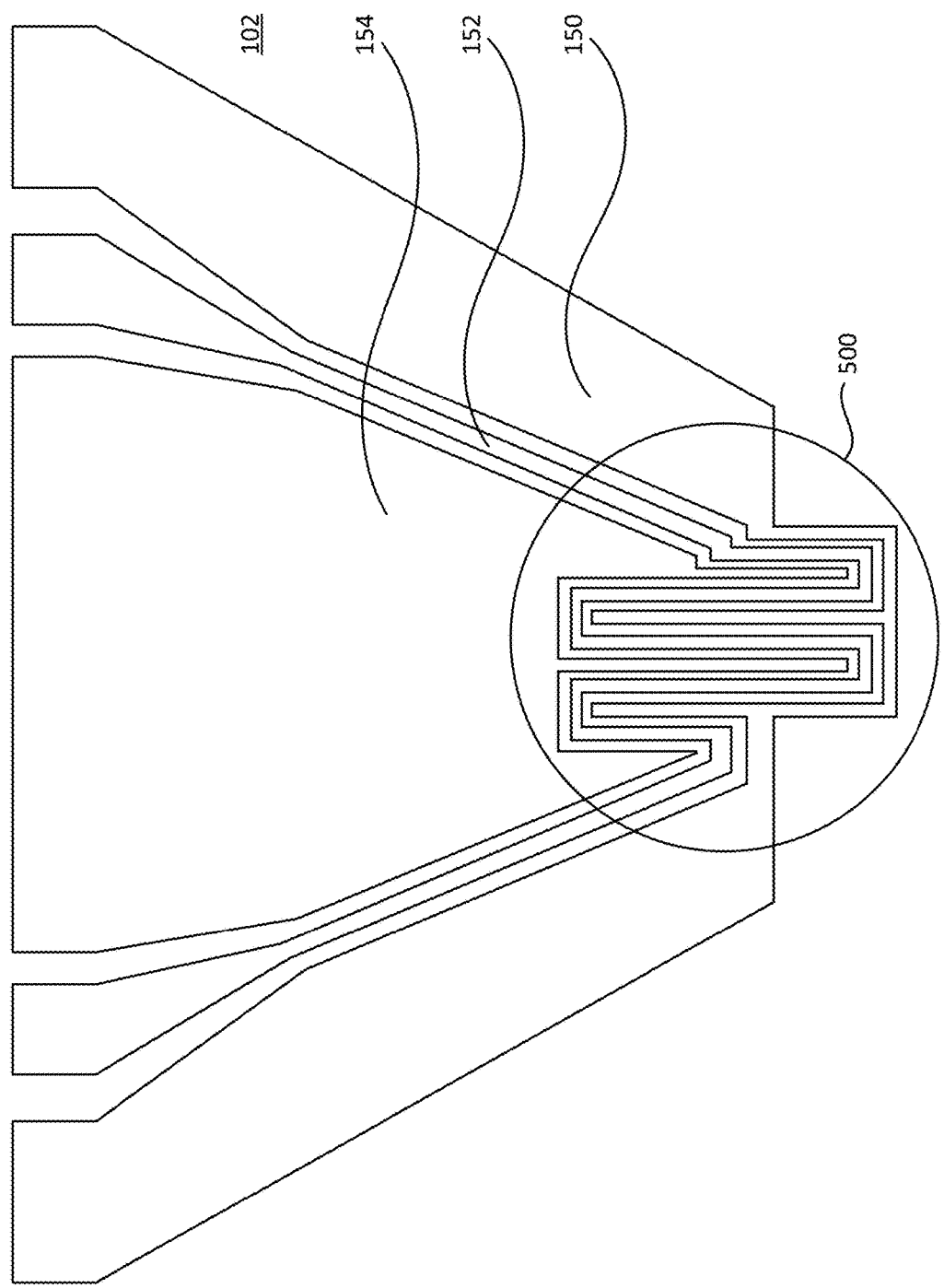
FIG. 21 shows a top view of a microwave probe that includes a dispersion compensation pattern.

A geometrical shape of primary shield electrode 150, transmission electrode 152, and secondary shield electrode 154 are effective to produce an electric field between and primary shield electrode 150 and transmission electrode 152 and also between transmission electrode 152 and secondary shield electrode 154. Primary shield electrode 150, transmission electrode 152, and secondary shield electrode 154 independently can have a linear shape, curved shape, and the like. The shape can be planar (e.g., within x-y plane shown in FIG. 4), or nonplanar (e.g., being present in more than one plane), and the like. According to an embodiment, first terminal shield electrode 164, terminal transmission electrode 172, and second terminal shield electrode 178 independently can have a non-linear shape as shown in FIG. 21 (a top view of microwave probe 102) and FIG. 22 (an enlarged view of a portion of microwave probe 102). Here, microwave probe 102 includes primary shield electrode 150, transmission electrode 152, and secondary shield electrode 154 that include dispersion compensation pattern 500 to compensate for dispersion of microwave radiation (e.g., sample microwave radiation 88 or probe microwave radiation 90) in first terminal shield electrode 164, terminal transmission electrode 172, or second terminal shield electrode 178. According to an embodiment, dispersion compensation pattern 500 of microwave probe 102 include an interdigitated pattern of first terminal shield electrode 164, terminal transmission electrode 172, and second terminal shield electrode 178 as shown in detail in FIG. 22.

Figure 22:
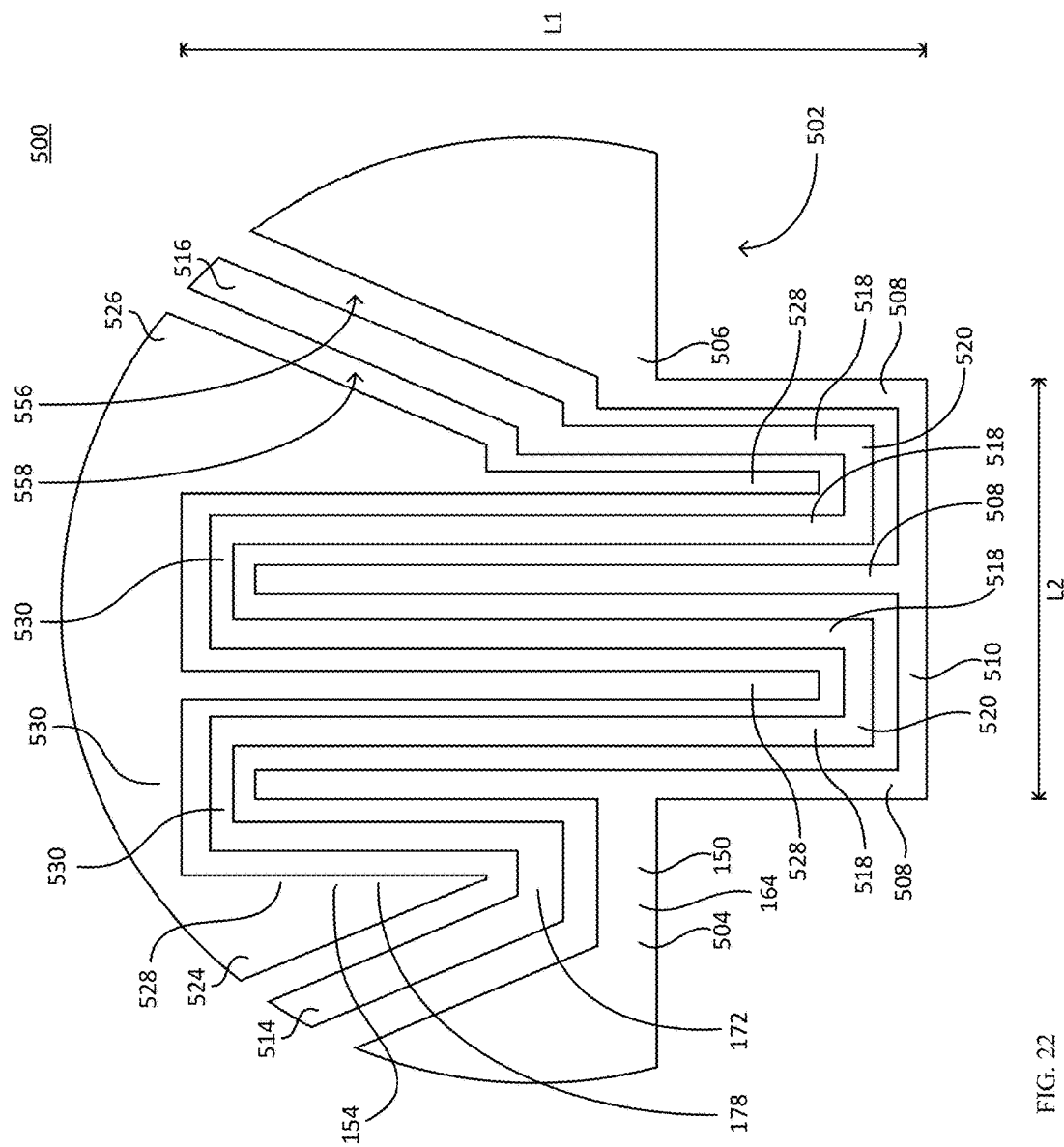
FIG. 22 shows an enlarged view of portion of the microwave probe that includes the dispersion compensation pattern shown in FIG. 21.

With reference to FIG. 22, dispersion compensation pattern 500 includes primary shield electrode 150, transmission electrode 152, secondary shield electrode 154 that span from input leg 501 to output leg 502. First terminal shield electrode 164 of primary shield electrode 150 includes input conductor 504 disposed at input leg 501 and output conductor 506 disposed at output leg 502. Input conductor 504 is in electrical communication with output conductor 526 via a plurality of span conductors 508 and traverse conductors 510.

Second terminal shield 178 electrode 164 secondary of primary shield electrode 154 includes input conductor 524 disposed at input leg 501 and output conductor 526 disposed at output leg 502. Input conductor 524 is in electrical communication with output conductor 526 via a plurality of span conductors 528 and traverse conductors 530.

Terminal transmission electrode 172 of transmission electrode 152 includes input conductor 514 disposed at input leg 501 and output conductor 516 disposed at output leg 502. Input conductor 514 is in electrical communication with output conductor 516 via a plurality of span conductors 518 and traverse conductors 520. Terminal transmission electrode 172 is electrically isolated from first terminal shield electrode 164 and spaced apart from first terminal shield electrode 164 by electrode gap 556. Additionally, terminal transmission electrode 172 is electrically isolated from second terminal shield electrode 178 and spaced apart from second terminal shield electrode 178 by electrode gap 558.

Although input conductor (504, 514, 524) and output conductor (506, 516, 526) are shown as planar and linear structures, the geometrical shape and arrangement of input conductor (504, 514, 524) and output conductor (506, 516, 526) can be any geometrical shape or arrangement effective to provide production of an electric field between transmission electrode 152 and primary shield electrode 150 and also between transmission electrode 152 and secondary shield electrode 154. Similarly, although span conductor (508, 518, 528) and traverse conductor (510, 520, 530) are shown as planar and linear structures arranged in an interdigitated pattern to compensate dispersion in microwave radiation (e.g., sample microwave radiation 88 or probe microwave radiation 90) propagating through transmission electrode 152, the geometrical shape in arrangement of span conductor (508, 518, 528) and traverse conductor (510, 520, 530) can be any geometrical shape or arrangement effective to compensate dispersion of microwave radiation (e.g., sample microwave radiation 88 or probe microwave radiation 90) in transmission electrode 152 and effective to provide production of an electric field between transmission electrode 152 and primary shield electrode 150 and also between transmission electrode 152 and secondary shield electrode 154.

Without wishing to be bound by theory, it is believed that a skin effect can effect communication of sample microwave radiation 88 or probe microwave radiation 90 in transmission electrode 152, wherein high frequency current can communicate preferentially at a surface of transmission electrode 152 relative to a bulk of transmission electrode 152. When communicated through a corner or bend (e.g., corner produced at an intersection of span conductor 518 and traverse conductor 520 in dispersion compensation pattern 500) of transmission electrode 152, high-frequency current (e.g., sample microwave radiation 88 or probe microwave radiation 90) experiences a current flow path length that can be different depending on which surface or corner in a bend of transmission electrode 152 through which the current flows. As a result, a dispersion can be produced as a phase shift in probe microwave radiation 90 (communicated from microwave probe 102 to interferometer 104) relative to reference microwave radiation 84 (communicated in reference arm 98) at power combiner 160. Advantageously, transmission electrode 152 having dispersion compensation pattern 500 decreases or eliminates the dispersion and provides suppression of such a background noise to increase sensitivity of phase shift detector 100. It is contemplated that a number of turns or counter turns can be equal numbers so that the current path length difference across transmission electrode 152 in dispersion compensation pattern 500 is minimized or absent. As a result, dispersion compensation pattern 500 provides dispersion control of communication of sample microwave radiation 88 and probe microwave radiation 90.

With reference to FIG. 8, FIG. 9, FIG. 10, FIG. 18, FIG. 19, FIG. 20, and FIG. 22, in an embodiment, substrate 160 supports primary shield electrode 150, transmission electrode 152, and secondary shield electrode 154 upon which they are disposed in whole or in part. A size, e.g., thickness T2, of substrate 160 can be selected to be large enough to support these components, to provide electrical isolation between these components as well as to mount microwave probe 102 on a mounting structure, e.g., a mounting structure configured to receive microwave probe 102 or to insert microwave probe 102 into interface coupler 350. Thickness T2 can be a largest linear dimension of substrate 160 and can be, e.g., from 10 micrometers (μm) to 10 centimeters (cm), specifically from 0.05 millimeters (mm) to 1 cm, and more specifically from 0.2 mm to 0.2 cm.

Thickness T1 of primary shield electrode 150, transmission electrode 152, and secondary shield electrode 154 independently can be from 0.002 micrometers (μm) to 0.5 centimeters (cm), specifically from 0.1 µm to 0.05 cm, and more specifically from 1 µm to 0.005 cm.

Width W1 of primary shield electrode 150 can be from 0.005 micrometers (µm) to 10 centimeters (cm), specifically from 0.00005 millimeters (mm) to 1 cm, and more specifically from 0.05 mm to 0.1 cm.

Width W2 of transmission electrode 152 can be from 0.005 micrometers (µm) to 0.5 centimeters (cm), specifically from 0.00005 millimeters (mm) to 0.1 cm, and more specifically from 0.05 mm to 0.03 cm.

Width W3 of secondary shield electrode 154 can be from 0.005 micrometers (µm) to 10 centimeters (cm), specifically from 0.0005 millimeters (mm) to 0.1 cm, and more specifically from 0.05 mm to 0.03 cm.

Width W4 of first electrode gap (156, 556) independently can be from 0.005 micrometers (µm) to 1 centimeters (cm), specifically from 0.0005 millimeters (mm) to 0.1 cm, and more specifically from 0.05 mm to 0.03 cm.

Width W5 of second electrode gap (158, 558) independently can be from 0.005 micrometers (µm) to 1 centimeters (cm), specifically from 0.0005 millimeters (mm) to 0.1 cm, and more specifically from 0.05 mm to 0.03 cm.

Width W8 of secondary shield electrode 154 can be from 10 micrometers (µm) to 50 centimeters (cm), specifically from 0.5 millimeters (mm) to 10 cm, and more specifically from 2 mm to 4 cm.

Width W11 of transmission electrode 152 can be from 0.01 micrometers (µm) to 100 centimeters (cm), specifically from 0.01 millimeters (mm) to 5 cm, and more specifically from 0.1 mm to 1 cm.

Length L1 of dispersion compensation pattern 500 can be from 1 micrometers (µm) to 10 centimeters (cm), specifically from 0.1 millimeters (mm) to 2 cm, and more specifically from 0.5 mm to 0.5 cm.

Length L2 of dispersion compensation pattern 500 can be from 0.01 micrometers (µm) to 10 centimeters (cm), specifically from 0.1 millimeters (mm) to 2 cm, and more specifically from 0.5 mm to 0.5 cm.

According to an embodiment, microwave probe 102 includes substrate 160 upon which transmission electrode 152, primary shield electrode 150, and secondary shield electrode 154 are disposed. Substrate 160 includes a material selected to isolate electrically transmission electrode 152 from primary shield electrode 150 and secondary shield electrode 154. In some embodiments, substrate 160 includes a material selected to transmit optically a wavelength of radiation such as infrared radiation, visible radiation, ultraviolet radiation, and the like. According to an embodiment, substrate 160 has a dielectric strength effective to isolate electrically transmission electrode 152 from primary shield electrode 150 and secondary shield electrode 154.

Exemplary materials for substrate 160 include electrically insulating materials.

In an embodiment, substrate 160 includes a plurality of layers or a single layer of material. In the plurality of layers, a laminate structure can be present that includes alternating layers of material, wherein individual layers can have a substantially similar or different composition.

In an embodiment, primary shield electrode 150, transmission electrode 152, secondary shield electrode 154 independently can include an electrically conductive material. Exemplary materials for electrodes (150, 152, 154) include copper, gold, aluminum, platinum, tungsten silicide, titanium nitride, and the like. High conductivity material can be used to minimize loss. In some embodiments, lower conductivity material can be used.

Figure 9:
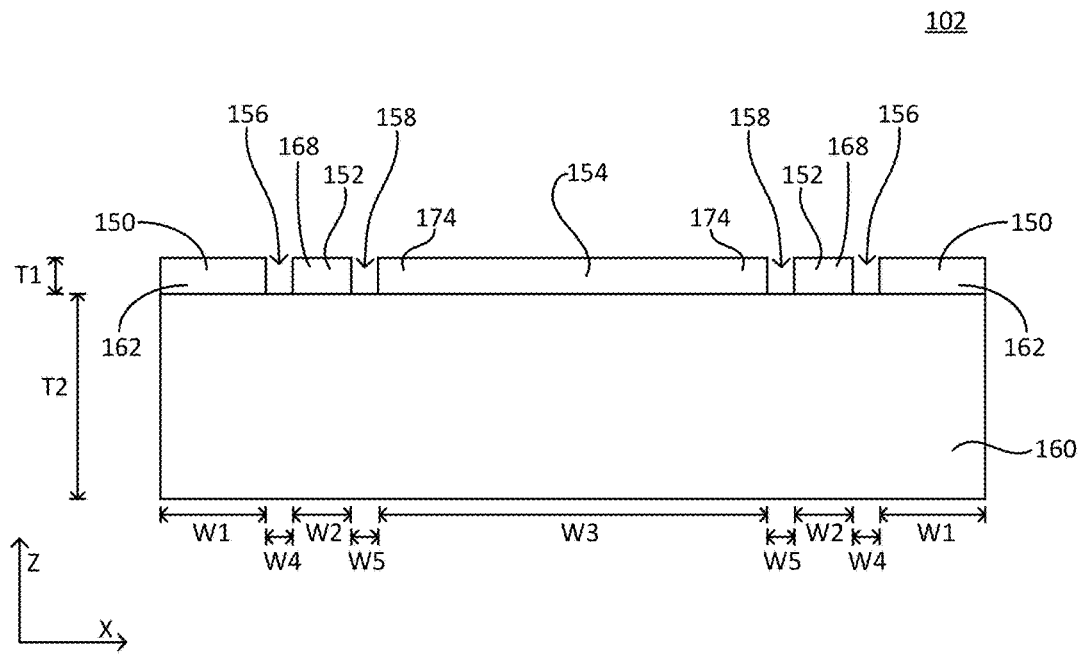
FIG. 9 shows a cross-section along line B-B of the microwave probe shown in FIG. 3.
Figure 10:
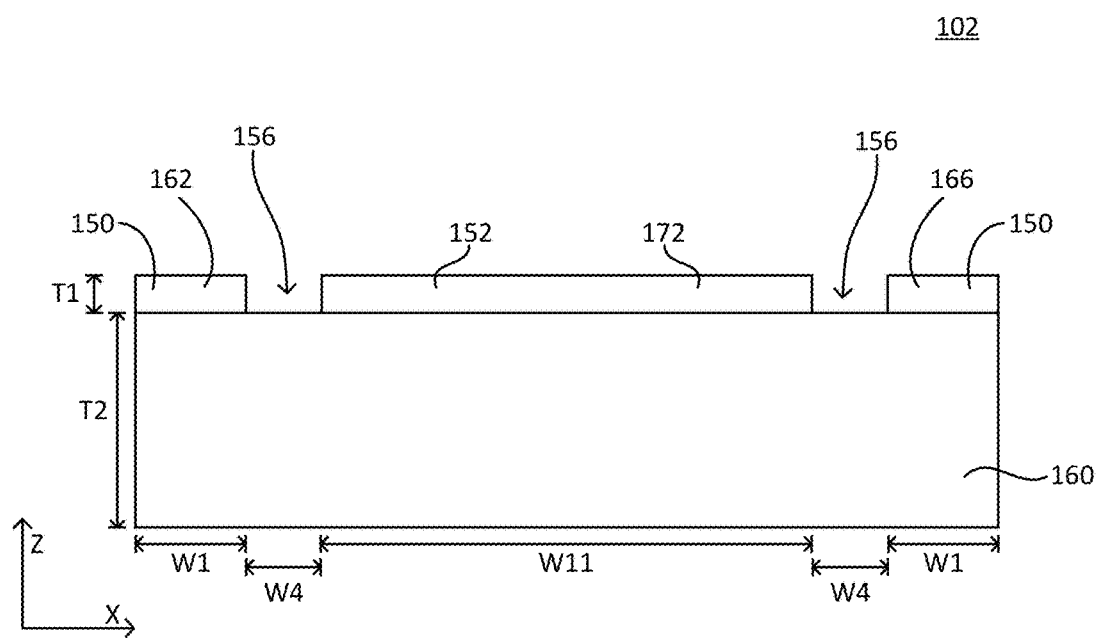
FIG. 10 shows a cross-section along line C-C of the microwave probe shown in FIG. 3.

In an embodiment, with reference to FIG. 9, FIG. 10, and FIG. 11, a process for making phase shift detector 100 includes providing connectorized components (e.g., a power splitter, phase shifter, attenuator, power combiner, and the like); connecting them together with semi-rigid microwave cables; measuring, with a spectrum analyzer, an output of the detector; and fine-tuning the phase or attenuation to achieve the best balance between the reference arm and the sample arm. In an embodiment, the two arms of interferometer 104 are adjusted as close to equal as possible so that the same microwave period is cancelling itself at the power combiner. As a result, source noise is substantially eliminated. Components can be mounted rigidly, and interferometer 104 is disposed in a temperature-controlled enclosure to avoid vibration and temperature variation induced phase variation. In a certain embodiment, components of phase shift detector 100 include chip components on a microwave printed circuit board to provide highly compact realization of phase shift detector 100 and including vibration dampening or elimination and temperature stabilization.

According to an embodiment, a process for making microwave probe 102 includes designing and fabricating a shadow mask of the layout of the microwave probe. Electrode material is deposited on the substrate through the shadow mask by evaporation. For very small probes, electrode material is deposited on the substrate first as blanket film. An electron beam (e-beam) resist is then spin coated. After e-beam direct write exposure and resist development, the electrode pattern is defined by dry etching. For electrode materials that are not amenable for dry etching, direct ion milling instead of e-beam lithography may be used.

Phase shift detector 100 advantageously can achieve extreme sensitivity in millimeter wave to radio wave range. When the wavelength is too short, such as optical wave, it is extremely difficult to finely balance to two arms. To adjust the path length at part per million level (to achieve better cancellation at the power combiner), optical wave with sub-micron wavelength can involve sub-picometer path length adjustment. For a wavelength in the millimeter or longer range, the path length adjustment is in the nanometer or longer range. When the wavelength is very long, the size of the system increases. In an embodiment, phase shift detector 100 operates with microwave radiation from 300 MHz to 300 GHz to provide a compact-sized system with high sensitivity. Moreover, phase shift detector 100 provides dispersion compensation in some embodiments. Phase shift detector 100 advantageously and surprisingly provides orders of magnitude better balance of the sample arm and reference arm than conventional bridged instruments and many orders of magnitude better sensitivity.

Phase shift detector 100 has beneficial and advantageous uses. In an embodiment, a process for acquiring phase shift data includes receiving microwave radiation 80 by power splitter 112; producing, by power splitter 112, reference microwave radiation 82 and sample microwave radiation 86; communicating reference microwave radiation 82 to reference arm 98; communicating sample microwave radiation 86 to sample arm 96; communicating sample microwave radiation 88 from sample arm 96 to a microwave probe, microwave probe 102 including substrate 106 including a dielectric, primary shield electrode 150 disposed on substrate 106, secondary shield electrode 154 opposingly disposed to primary shield electrode 150, and transmission electrode 152 interposed between primary shield electrode 150 and secondary shield electrode 154, transmission electrode 152 being isolated electrically from primary shield electrode 150 and isolated electrically from secondary shield electrode 154; subjecting, by microwave probe 102, a sample to sample microwave radiation 88; producing, by microwave probe 102, probe microwave radiation 90 in response to subjecting the sample to sample microwave radiation 88; communicating probe microwave radiation 90 in sample arm 96 to power combiner 116; receiving, by power combiner 116, probe microwave radiation 90 and reference microwave radiation 84 from reference arm 98; and producing, by power combiner 116, interferometer signal 92 in response to receiving probe microwave radiation 90 and reference microwave radiation 84 to acquire phase shift data. The process can further include shifting a phase of reference microwave radiation 82 prior to power combiner 116 receiving reference microwave radiation 84 from reference arm 98. According to an embodiment, the process also includes attenuating a power of sample microwave radiation 86 prior to subjecting the sample to sample microwave radiation 88. In an embodiment, phase shift detector 104 is operated in this manner to acquire phase shift data.

Figure 23:
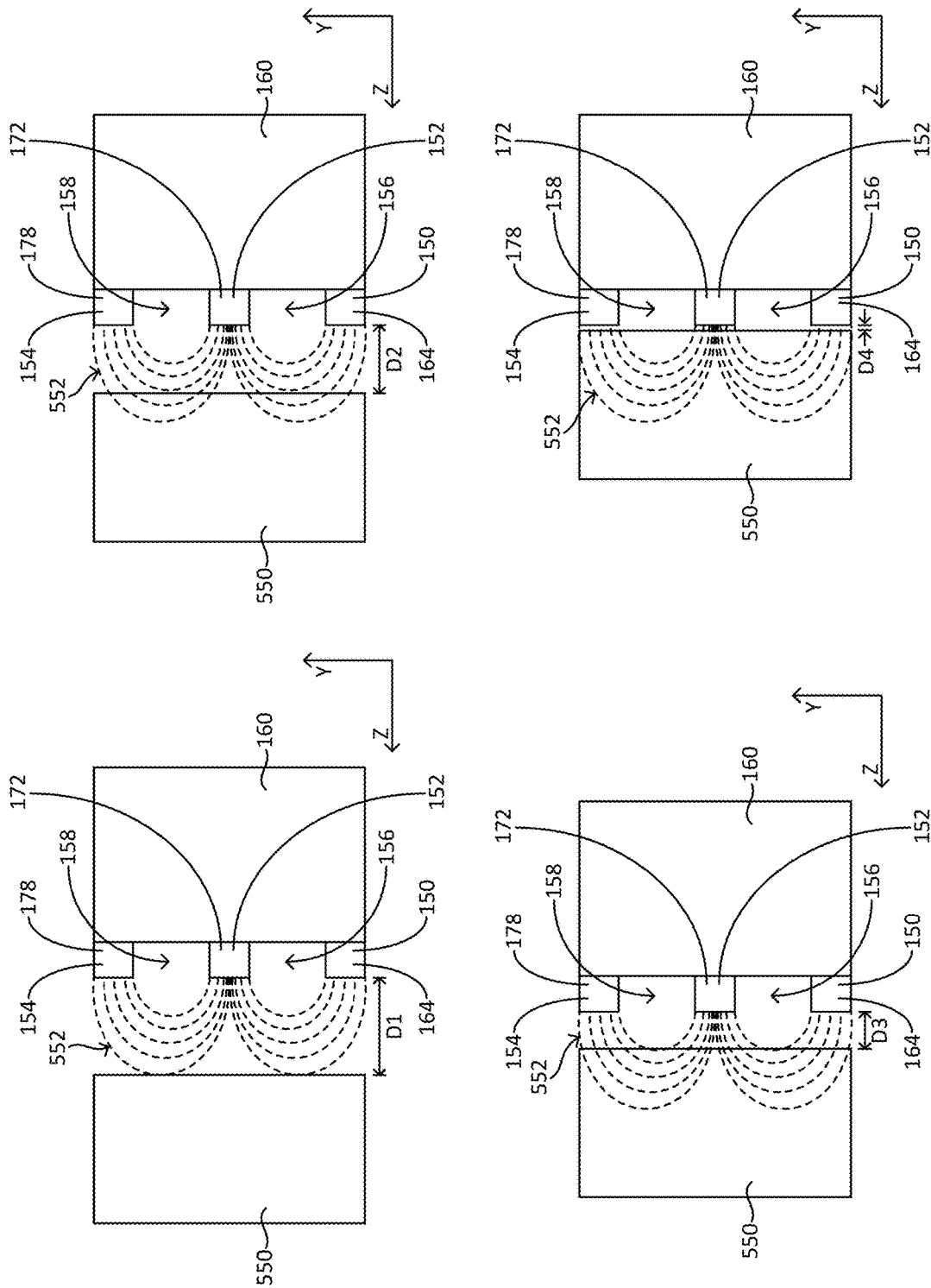
FIG. 23 shows a microwave probe disposed proximate to a sample at a plurality of distances.

In an embodiment, as shown in FIG. 23 (which shows a cross-sectional view of microwave probe 102 (similar to that shown in FIG. 8)) disposed proximate to 550 at a plurality of distances (D1, D2, D3, D4)), sample 550 is disposed at first distance D1 from microwave probe 102. At first distance D1, sample 550 is not disposed in electric field 552 formed by sample microwave radiation 88 communicated in transmission electrode 152 relative to primary shield electrode 150 and secondary shield electrode 154. Here, electric field 552 has a magnitude proportional to a difference in electrical potential of transmission electrode 152 relative to primary shield electrode 150 and secondary shield electrode 154 such that transmission electrode 152 communicates sample microwave radiation 88 in an effective dielectric constant. Sample microwave radiation 88 that is communicated to transmission electrode 152 from interferometer 104, produces electric field 552 at first terminal shield electrode 164, terminal transmission electrode 172, and second terminal shield electrode 178. Probe microwave radiation 90 is produced as a result of interaction of electric field 552 with sample 550 and is communicated through terminal transmission electrode 172 and other components of transmission electrode 152 to second transmission member 106 of interferometer 104. In an absence of sample 550 in electric field 552, a probe microwave radiation 90 is identical to sample microwave radiation 88. In a presence of sample 550, electric field 552 is perturbed due to a dielectric constant of sample 550, and probe microwave radiation 90 is different from some form microwave radiation 88 in a phase or power. It is contemplated that in a presence of sample 550 in electric field 552, sample microwave radiation 88 has a first phase and third power, but probe microwave radiation 90 is a third phase in fourth power, wherein a difference in the first phase in the third phase is detected via heterodyne detection at the power combiner 116 in relation to reference microwave radiation 84, which has a second phase and first power. Again, if probe microwave radiation 90 is identical to sample microwave radiation 88, then they will have identical phases and powers, such that the third phase and first phase will be identical and the third power and fourth power be identical.

In an embodiment, interferometer 104 is a Mach-Zehnder interferometer that includes impedance-controlled transmission lines (120, 122, 124, 126, 128). Also, power splitter 112, power combiner 116, phase shifter 114, and attenuator 118 (e.g., a variable attenuator) can have inputs and outputs that are impedance matched to transmission lines (120, 122, 124, 126, 128). In interferometer 104, reference arm 98 and sample arm 96 can have electrical path lengths that are within one-half of an electrical wavelength so that when interferometer 104 is electrically balanced, the same microwave cycle of reference microwave radiation 84 and probe microwave radiation 90 is self-canceling. Further, microwave probe 102 includes electrodes (150, 152, 154) that are generally not impedance matched to transmission lines (120, 122, 124, 126, 128, 105, 106). In an embodiment, primary shield electrode 150, transmission electrode 152, secondary shield electrode 154 are exposed parallel metallic conductors to provide electric field 552 with electric field lines arranged to be intercepted by sample 550 so that sample 550 changes the effective dielectric constant experience by sample microwave radiation 88 to produce a probe microwave radiation 90. It is contemplated that electrodes (150, 152, 154) have electrical path length that is less than or equal to one-quarter of the electrical path wavelength of sample microwave radiation 88.

According to an embodiment, a process for operating phase shift detector 100 includes: balancing interferometer 104 by adjusting phase shifter 114 or adjusting attenuator 118; disposing sample 550 proximate to transmission electrode 152 at a distance so that sample 550 intercepts electric field 552; re-balancing interferometer 104 by adjusting phase shifter 114 or attenuator 118; and producing interferometer signal 92, wherein interferometer signal 92 has a magnitude that changes due to a change in a property of sample 550. The property of sample 550 includes, e.g., a dielectric constant, temperature, microwave absorption, and the like.

Referring again to FIG. 23, at first distance D1, electric field 552 is produced in an absence of disposition of sample 550 therein while at second distance D2 (which is less than first distance D1), sample 550 is disposed in electric field 552 such that a presence of sample 550 in electric field 552 effects electric field 552, wherein transmission electrode 152 communicates sample microwave radiation 88 in a different effective dielectric constant, and the balance of interferometer 104 is changed so that a level of interferometer signal 92 is changed. Removing sample 550 closer to microwave probe 102 from second distance D2 to third distance D3 and then closer to fourth distance D4 (wherein D1>D2>D3>D4), produces in imbalance between reference arm 98 and sample arm 96 in interferometer 104 has the distance D between sample 550 and microwave probe 102 varies. It is contemplated that interferometer 104 can be re-balanced by adjusting phase shifter 114 or attenuator 118. Moreover, in addition to a change in a distance D between microwave probe 102 and sample 550 (i.e., a position along z-axis shown in FIG. 23) be changed as interferometer signal 92 is monitored, a position of sample 550 relative to microwave probe 102 along the x-axis or y-axis can be varied as interferometer signal 92 is monitored. In this manner, phase shift data a can be acquired as microwave probe 102 scans over a surface of sample 550 as a function of distance therefrom, and interferometer signal 92 can be analyzed to determine the property of the sample, e.g., temperature, dielectric constant, and the like.

Figure 24:
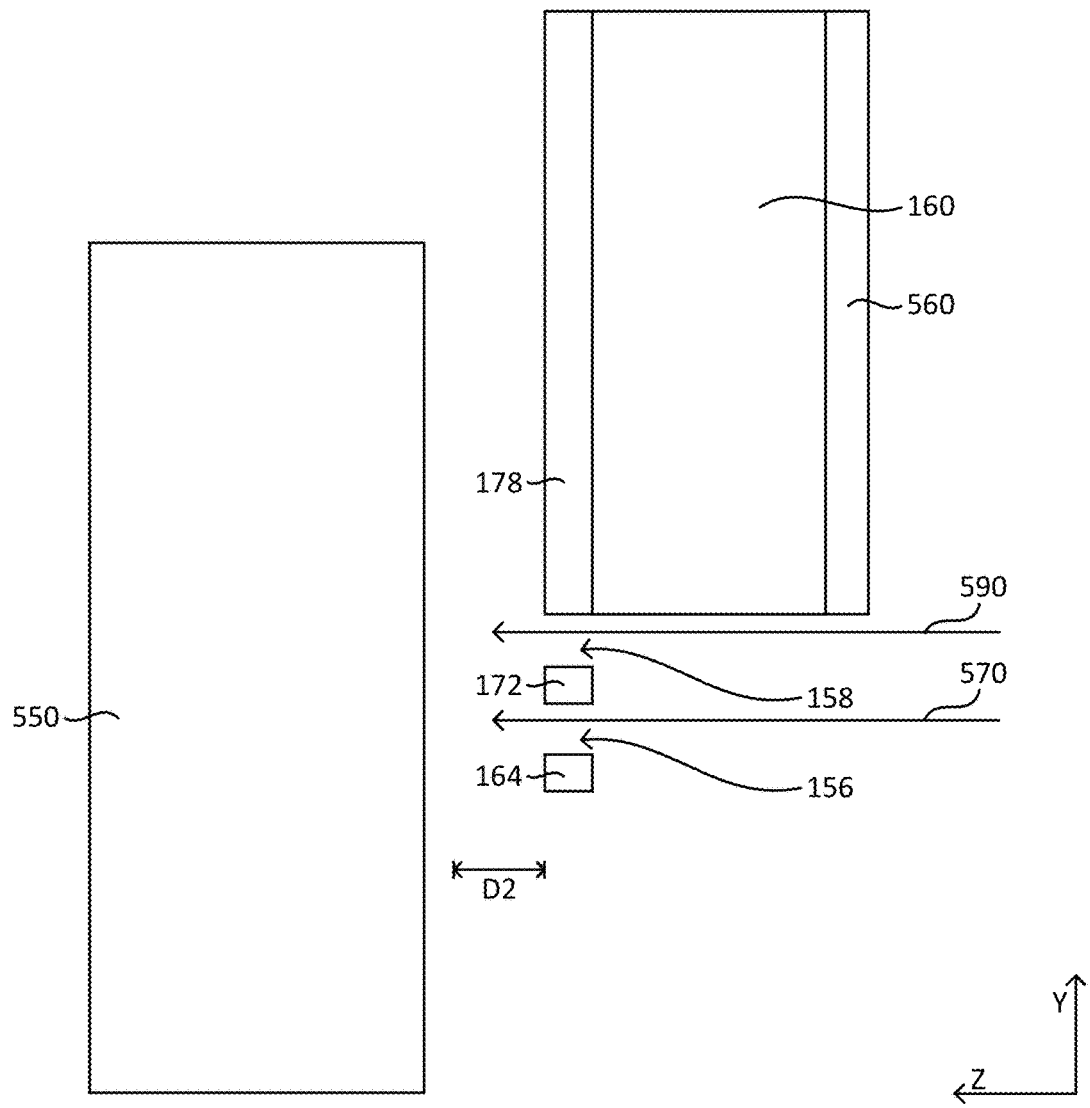
FIG. 24 shows a microwave probe disposed proximate to a sample.
Figure 25:
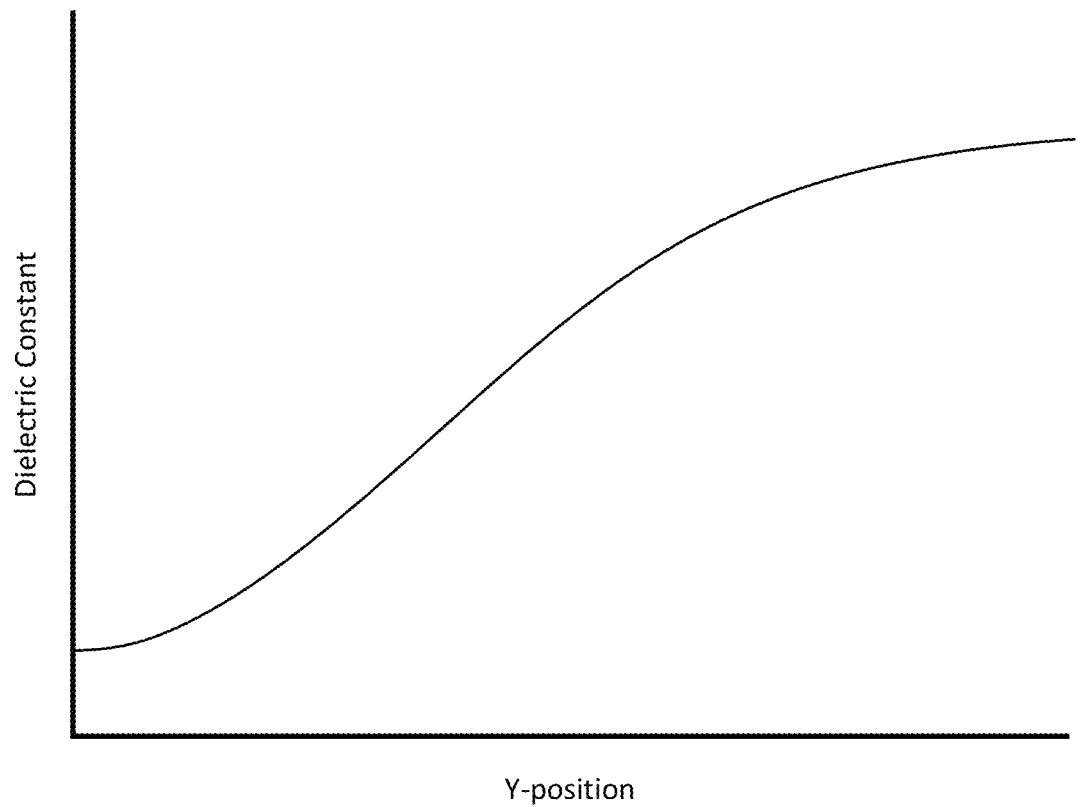
FIG. 25 shows a graph of dielectric constant versus a position of the microwave probe relative to the sample shown in FIG. 24.

In an embodiment, as shown in FIG. 24, microwave probe 102 (similar to microwave probe 102 shown in FIG. 18) is disposed proximate to sample 550, and radiation 570 (e.g., infrared radiation) is directed from a radiation source to microwave probe 102 and is transmitted through first electrode gap 156 or second electrode gap 158. Sample 550 is subjected to radiation 570 transmitted first electrode gap 156 or second electrode gap 158. Here, a position of sample 550 relative to microwave probe 102 can be changed while communicating the sample microwave radiation 88 to terminal transmission electrode 172 and producing probe microwave radiation 88 that is communicated to sample arm 96 of interferometer 104 while monitoring interferometer signal 92 to determine a property of sample 550. According to an embodiment, the property is the dielectric constant of sample 550, and FIG. 25 shows a graph of dielectric constant versus a y-axis position of microwave probe 102 relative to sample 550. Here, the dielectric constant of sample 550 increases as the y-position of microwave probe 102 is change relative to sample 550.

According to an embodiment, phase shift detector 100 is interfaced with a Fourier transform infrared spectrometer and increases a sensitivity of Fourier transform infrared spectroscopy by communicating infrared radiation from the first electrode gap 156 or second electrode gap 158 of microwave probe 102. In a certain embodiment, phase shift detector 100 is used to detect a temperature change or temperature change profile of sample 550, and interferometer signal 92 has a high temperature sensitivity (e.g., 0.001° C. and the like), spatial resolution (e.g., 0.005 micrometer (μm)), or temporal resolution (e.g., 0.005 nanoseconds (ns)) for infrared absorption property determination for sample 550. It is contemplated that a size or geometrical shape of microwave probe 102 can be selected to provide a desired spatial resolution of the property measured by phase shift detector 100.

According to an embodiment, phase shift detector 100 is used as a temperature probe with high spatial resolution and high speed. Using a micro fabricated microwave probe 102, microwave radiation in electrode gaps 156 and 158 interact with the sample 550 locally. In a certain embodiment, phase shift detector 100 is used to detect a local temperature change of sample 550, and interferometer signal 92 has a high temperature sensitivity (e.g., 0.001° C. and the like), spatial resolution (e.g., 0.005 micrometer (μm)), or temporal resolution (e.g., 0.005 nanoseconds (ns)) for thermometry or electrical property determination for sample 550. It is contemplated that a size or geometrical shape of microwave probe 102 can be selected to provide a desired spatial resolution of the property measured by phase shift detector 100.

According to an embodiment, phase shift detector 100 is used as an acoustic probe with high sensitivity and high speed. Using a microwave probe 102, microwave radiation in electrode gaps 156 and 158 interact with the sample 550. In a certain embodiment, phase shift detector 100 is used to detect a change of distance between sample 550 and probe 102, and interferometer signal 92 has a high distance sensitivity (e.g., 0.1 nm and the like), spatial resolution (e.g., 0.005 micrometer (μm)), or temporal resolution (e.g., 0.005 nanoseconds (ns)) for acoustic vibration of sample 550. It is contemplated that a size or geometrical shape of microwave probe 102 can be selected to provide a desired vibration magnitude resolution of the sample measured by phase shift detector 100.

The articles and processes herein are illustrated further by the following Examples, which are non-limiting.

EXAMPLES

Example 1. Sensitivity to Local Dielectric Constant Change Via Distance Modulation A phase shift detector was provided, and the arms of the interferometer were balanced in an absence of a sample. The microwave probe was brought in proximity to an aluminum surface. As the surface got closer to the microwave probe, the local dielectric constant changed, and the bridge became unbalanced. The bridge output (unbalanced) was used to monitor the distance between the microwave probe and the aluminum surface. The functional form of this relationship depended on the microwave probe geometry and material composition. The resulting distance dependence is shown in FIG. 26.

Figure 26:
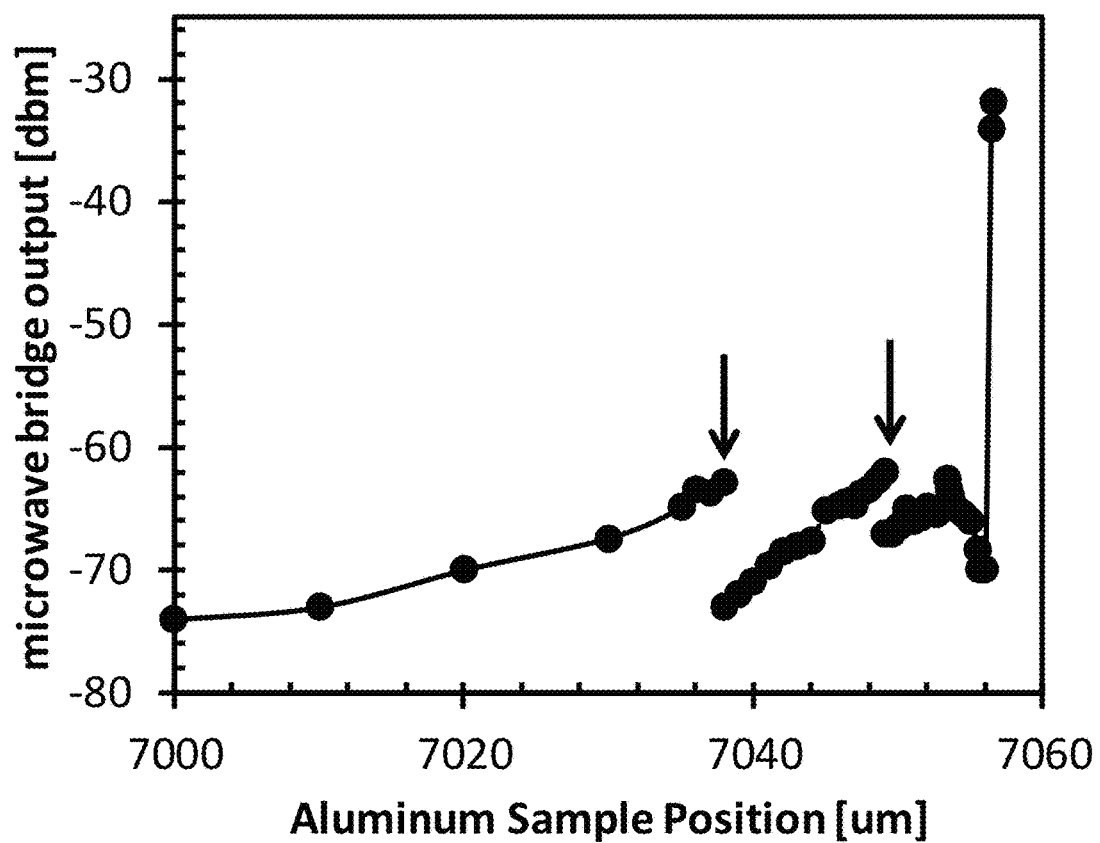
FIG. 26 shows a graph of microwave bridge output versus aluminum sample position according to Example 1.

With regard to FIG. 26, the aluminum position scale was arbitrarily offset. As the aluminum surface was brought closer to the microwave probe, the microwave bridge was periodically re-balanced to improve sensitivity (marked with arrows). After re-balancing, the aluminum surface to microwave probe distance was further reduced. As the distance was minimized, the microwave bridge output response became more pronounced. As the probe was finally brought into contact with the aluminum surface, the microwave bridge output underwent a sharp change that indicated touchdown and contact therebetween.

Example 2. Sensitivity to Local Dielectric Constant Change Via Temperature Modulation A phase shift detector was provided, and the microwave probe was brought in close proximity to a heat source. A heat source changed the local temperature of the microwave probe and its surroundings. The change in local temperature resulted in a local dielectric constant change, which unbalances the bridge. The exact functional form of this temperature to microwave bridge output relationship depended on the microwave probe geometry and material composition. The resulting distance dependence is shown in FIG. 27.

Figure 27:
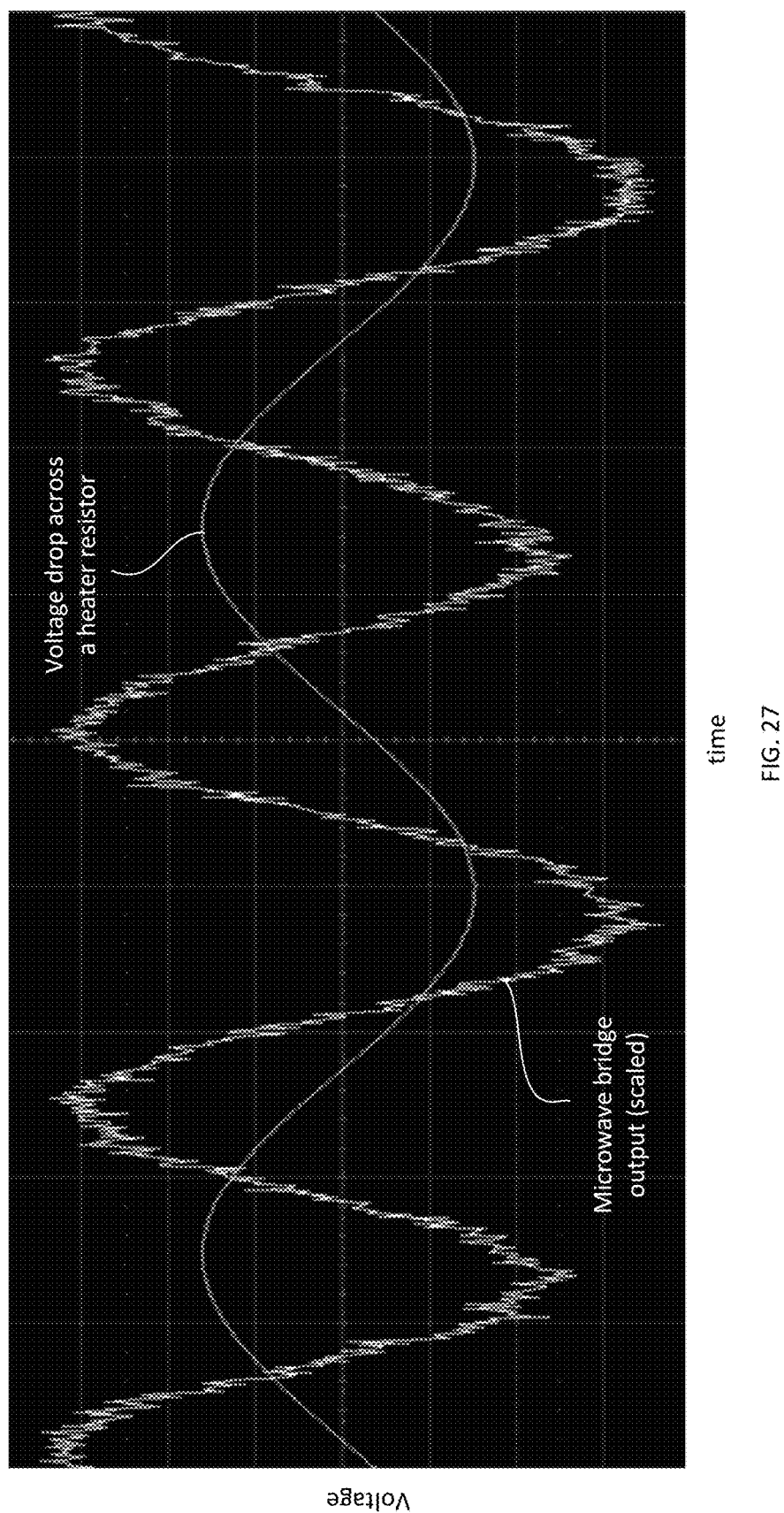
FIG. 27 shows a graph of voltage versus time from oscilloscope traces according to Example 2.

The heat source was quantified by measuring the voltage drop across a heating element (marked in FIG. 27). The temperature modulation in this example is less than 0.5° C. The resultant microwave bridge output range (also marked in FIG. 27) corresponded to approximately −55 dBm to −45 dBm. The microwave bridge output followed the heat source temperature modulation. The phase between the voltage drop across the heater resistor signal and the bridge output signal was arbitrary.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A phase shift detector comprising:
    an interferometer to receive a microwave radiation; and
    a microwave probe in electrical communication with the interferometer to receive a sample microwave radiation from the interferometer and to produce a probe microwave radiation, the microwave probe comprising:
    a primary shield electrode; and
    a transmission electrode disposed proximate to the primary shield electrode, the transmission electrode and the primary shield electrode being exposed and arranged to produce an electric field in response to receipt of the sample microwave radiation by the transmission electrode,
    where the transmission electrode is isolated electrically from the primary shield electrode,
    wherein the microwave probe further comprises a secondary shield electrode disposed proximate to the transmission electrode,
    wherein the transmission electrode is interposed between the secondary shield electrode and the primary shield electrode, and
    wherein the transmission electrode is isolated electrically from the secondary shield electrode.

2. The phase shift detector of claim 1, wherein the secondary shield electrode is exposed and arranged to produce an electric field between the secondary shield electrode and the transmission electrode in response to receipt of the sample microwave radiation by the transmission electrode.

3. The phase shift detector of claim 2, wherein the microwave probe further comprises a substrate upon which the transmission electrode, the primary shield electrode, and the secondary shield electrode are disposed.

4. The phase shift detector of claim 3, wherein the interferometer comprises:
    a power splitter to receive the microwave radiation, to produce a reference microwave radiation from the microwave radiation, and to produce the sample microwave radiation from the microwave radiation;
    a reference arm in electrical communication with the power splitter to receive the reference microwave radiation; and
    a sample arm in electrical communication with the power splitter to receive the sample microwave radiation and to communicate the sample microwave radiation to the microwave probe,
    wherein the reference microwave radiation comprises:
    a first phase; and
    a first power, and
    the sample microwave radiation comprises:
    the first phase; and
    a second power.

5. The phase shift detector of claim 4, wherein the reference arm comprises a phase shifter:
    to receive the reference microwave radiation comprising the first phase;
    to shift the first phase to a second phase; and
    to communicate the reference microwave radiation comprising the second phase.

6. The phase shift detector of claim 5, wherein the sample arm comprises an attenuator:
    to receive the sample microwave radiation comprising the second power;
    to attenuate the second power to a third power; and
    to communicate the sample microwave radiation comprising the third power to the microwave probe.

7. The phase shift detector of claim 6, wherein the sample arm further comprises a first transmission member electrically interposed between the attenuator and the microwave probe and in electrical communication with the attenuator to provide the sample microwave radiation to the microwave probe.

8. The phase shift detector of claim 7, wherein the first transmission member comprises:
    a first central conductor to receive the sample microwave radiation from the attenuator and in electrical communication with the transmission electrode of the microwave probe to communicate the sample microwave radiation to the transmission electrode;
    a first shield conductor surroundingly disposed about the first central conductor and in electrical communication with the primary shield electrode of the microwave probe; and
    a first dielectric sheath interposed between the first central conductor and the first shield conductor to isolate electrically the first central conductor from the first shield conductor.

9. The phase shift detector of claim 8, wherein the sample arm further comprises a second transmission member in electrical communication with the microwave probe to receive the probe microwave radiation from the microwave probe.

10. The phase shift detector of claim 9, wherein the second transmission member comprises:
    a second central conductor in electrical communication with the transmission electrode of the microwave probe;
    a second shield conductor surroundingly disposed about the second central conductor and in electrical communication with the secondary shield electrode of the microwave probe; and a second dielectric sheath interposed between the second central conductor and the second shield conductor to isolate electrically the second central conductor from the second shield conductor.

11. The phase shift detector of claim 10, wherein the interferometer further comprises a power combiner in electrical communication with the reference arm and the sample arm to receive the reference microwave radiation from the reference arm and to receive the probe microwave radiation from the second transmission member.

12. The phase shift detector of claim 11, wherein the transmission electrode of the microwave probe comprises a dispersion compensation pattern.

13. The phase shift detector of claim 12, wherein the transmission electrode of the microwave probe comprises an interdigitated pattern of the first terminal shield electrode, the terminal transmission electrode, and the second terminal shield electrode.

14. The phase shift detector of claim 12, further comprising an interface coupler electrically interposed between the sample arm and the microwave probe.

15. The phase shift detector of claim 13, wherein the interferometer comprises a Mach-Zehnder interferometer.

16. A phase shift detector comprising:
an interferometer comprising:
   a power splitter;
   a reference arm in electrical communication with the power splitter and comprising a phase shifter;
   a sample arm in electrical communication with the power splitter and comprising an attenuator; and
   a power combiner in electrical communication with the reference arm and the sample arm; and
a microwave probe in electrical communication with the sample arm and the power combiner, the microwave probe comprising:
   a substrate comprising a dielectric;
   a primary shield electrode disposed on the substrate;
   a secondary shield electrode opposingly disposed to the primary shield electrode; and
   a transmission electrode interposed between the primary shield electrode and the secondary shield electrode,
wherein the transmission electrode is isolated electrically from the primary shield electrode and isolated electrically from the secondary shield electrode.

* * * * *